US011744819B2

(12) United States Patent
Thompson et al.

(10) Patent No.: US 11,744,819 B2
(45) Date of Patent: *Sep. 5, 2023

(54) ANTIBIOTIC CANNABINOID-TERPENE FORMULATIONS

(71) Applicant: The University of British Columbia, Vancouver (CA)

(72) Inventors: Charles J. Thompson, Vancouver (CA); Mark C. Pryjma, Ajax (CA); Dana M. Lambert, West Vancouver (CA); Manisha Dosanjh, Surrey (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/589,588

(22) Filed: Jan. 31, 2022

(65) Prior Publication Data

US 2022/0233494 A1 Jul. 28, 2022

Related U.S. Application Data

(63) Continuation of application No. 17/607,247, filed as application No. PCT/CA2020/050613 on May 6, 2020.

(60) Provisional application No. 62/843,687, filed on May 6, 2019.

(51) Int. Cl.

| | |
|---|---|
| *A01N 37/18* | (2006.01) |
| *A61K 38/04* | (2006.01) |
| *A61K 38/12* | (2006.01) |
| *A61K 38/14* | (2006.01) |
| *A61K 31/352* | (2006.01) |
| *A61K 31/05* | (2006.01) |
| *A61K 45/06* | (2006.01) |
| *A61P 31/04* | (2006.01) |
| *A61K 31/015* | (2006.01) |
| *A61K 31/00* | (2006.01) |

(52) U.S. Cl.
CPC .......... *A61K 31/352* (2013.01); *A61K 31/015* (2013.01); *A61K 31/05* (2013.01); *A61K 31/658* (2023.05); *A61K 38/12* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 6,630,507 | B1 | 10/2003 | Hampson et al. |
| 7,323,576 | B2 | 1/2008 | Souza et al. |
| 2016/0250270 | A1 | 9/2016 | Wendschuh et al. |
| 2018/0344661 | A1 | 12/2018 | Finley et al. |
| 2022/0218654 | A1 * | 7/2022 | Thompson .............. A61K 31/05 |

FOREIGN PATENT DOCUMENTS

| | | | |
|---|---|---|---|
| EP | 3261629 | 1/2018 | |
| WO | WO 2012/012498 | 1/2012 | |
| WO | WO 2018/011813 | 1/2018 | |
| WO | WO 2018/234301 | 12/2018 | |
| WO | WO-2018234301 A1 * | 12/2018 | ............. A61K 31/05 |
| WO | WO 2019/198056 | 10/2019 | |
| WO | WO 2020/000024 | 1/2020 | |
| WO | WO 2020/051284 | 3/2020 | |

OTHER PUBLICATIONS

"Treat", Medical Dictionary, available online at https://medical-dictionary.thefreedictionary.com/treat, 3 pages (2012) (Year: 2012).*
Scull et al., Appl. Microbiol. Biotechnol. 104:7853-7865 (2020) (Year: 2020).*
Lin et al., Bioorganic Med. Chem. Lett. 27:456-459 (2017) (Year: 2017).*
Carpenter et al., Rev. Anti-Infective Agents 38:994-1000 (2004) (Year: 2004).*
"Daptomycin Injection," Natl. Inst. Health, available online at https://medlineplus.gov/druginfo/meds/a608045.html, 4 pages (2019) (Year: 2019).*
Hirsch, A., "Daptomycin (CubicinT): A New Treatment Option from Gram-Positive Infections," Cleveland Clinic, Pharmacotherapy Update, vol. 7, 5 pages (2004) (Year: 2004).*
"Types of Microbes", The National Academy of Sciences, available online at http://needtoknow.nas.edu/id/infection/microbe-types/, 2 pages (2022) (Year: 2022).*
Karas et al., Antibiotics 9:10 pages (2020) (Year: 2020).*
Taylor, M., "Antibiotic Compound in Cannabis Fights Gram-positive and Gram-negative Bacteria," available online at www.laboratoryequipment.com/561237-Antibiotic-Compound-in-Cannabis-Fights-Gram-positive-and-Gram-negative-Bacteria/, 7 pages (2020) (Year: 2020).*
Abdelaziz, A., (1983) Studies on the antimicrobial activity of cannabinoids. MS thesis, Ohio State University.
André, C. M.; Hausman, J.-F.; Guerriero, G. (2016). "Cannabis sativa: The Plant of the Thousand and One Molecules". Frontiers in Plant Science. 7: 19.

(Continued)

*Primary Examiner* — Thea D' Ambrosio
(74) *Attorney, Agent, or Firm* — BOZICEVIC FIELD & FRANCIS, LLP; Paula A. Borden

(57) ABSTRACT

Pharmaceutical formulations are provided that include at least two antibiotically active ingredients: a cannabinoid that is one or more of cannabichromene (CBC), cannabidiol (CBD) and/or cannabigerol (CBG); a sesquiterpene that is one or both of a-humulene and/or β-caryophyllene; and a lipopeptide antibiotic that is daptomycin or an analogue thereof. The antibiotically active ingredients may be provided in relative amounts that amplify their individual activities, including amounts that are synergistically effective in an assay to inhibit growth and/or reproduction of an *Enterococcus faecium* or an *Enterococcus faecalis*. Therapies are provided that utilize these formulations as antimicrobials, and provide for the combined use of two or more of the antibiotically active compounds.

8 Claims, 10 Drawing Sheets

(56) References Cited

OTHER PUBLICATIONS

Appendino, G., G. Chianese & 0. Taglialatela-Scafati, (2011) Cannabinoids: occurrence and medicinal chemistry. Curr Med Chem 18:10854099.

Appendino, G., S. Gibbons, A. Giana, A. Pagani, G. Grassi, M. Stavri, E. Smith & M.M. Rahman, (2008) Antibacterial cannabinoids from Cannabis sativa: a structure-activity study. J Nat Prod 71: 1427-1430.

Arias, C.A. & B.E. Murray, (2012) The rise of the Enterococcus: beyond vancomycin resistance. Nat Rev Microbiol 10: 266-278.

Arias et al, (2011) Genetic basis for in vivo daptomycin resistance in enterococci. N Engl.' Med 365: 892-900.

Arthur, M. & P. Courvalin, (1993) Genetics and mechanisms of glycopeptide resistance in enterococci. Antimicrob Agents Chemother 37: 1563-1571.

Avery, Lindsay M et al. "Pharmacodynamic Analysis of Daptomycin-treated Enterococcal Bacteremia: It Is Time to Change the Breakpoint." Clinical Infectious Diseases vol. 68,10 (2019): 1650-1657.

Baltz RH (Dec. 2006). "Molecular engineering approaches to peptide, polyketide and other antibiotics". Nature Biotechnology. 24 (12): 1533-40.

Berenbaum, M. C. 1978. A method for testing for synergy with any number of agents. J. Infect. Dis. 137:122-130.

Consroe, P., J. Laguna, J. Allender, S. Snider, L. Stern, R. Sandyk, K. Kennedy & K. Schram, (1991) Controlled clinical trial of cannabidiol in Huntington's disease. Pharmacol Biochem Behav 40: 701-708.

Cunha, J.M., E.A. Carlini, A.E. Pereira, O.L. Ramos, C. Pimentel, R. Gagliardi, W.L. Sanvito, N. Lander & R. Mechoulam, (1980) Chronic administration of cannabidiol to healthy volunteers and epileptic patients. Pharmacology 21: 175-185.

Dvorchik, Barry H et al. "Daptomycin pharmacokinetics and safety following administration of escalating doses once daily to healthy subjects." Antimicrobial agents and chemotherapy vol. 47,4 (2003): 1318-23. doi :10.1128/aac.47.4.1318-1323.2003.

Eisohly, H.N., C.E. Turner, A.M. Clark & M.A. Eisohly, (1982) Synthesis and antimicrobial activities of certain cannabichromene and cannabigerol related compounds. J Pharm Sci 71: 1319-1323.

Galloway-Pena, J.R., S.R. Nallapareddy, C.A. Arias, G.M. Eliopoulos & B.E. Murray, (2009) Analysis of clonality and antibiotic resistance among early clinical isolates of Enterococcus faecium in the United States. J Infect Dis 200: 1566-1573.

Hidron, A.I., J.R. Edwards, J. Patel, T.C. Horan, D.M. Sievert, D.A. Pollock, S.K. Fridkin, T. National Healthcare Safety Network & F. Participating National Healthcare Safety Network, (2008) NHSN annual update: antimicrobial-resistant pathogens associated with healthcare-associated infections: annual summary of data reported to the National Healthcare Safety Network at the Centers for Disease Control and Prevention, 2006-2007. Infect Control Hosp Epidemiol 29: 996-1011.

Luo X, Reiter MA, d'Espaux L, Wong J, Denby CM, Lechner A, Zhang Y, Grzybowski AT, Harth S, Lin W, Lee H, Yu C, Shin J, Deng K, Benites VT, Wang G, Baidoo EEK, Chen Y, Dev I, Petzold CJ, Keasling JD. 2019. Complete biosynthesis of cannabinoids and their unnatural analogues in yeast. Nature 567:123-126.

Mechoulam, R. & Y. Gaoni, (1965) Hashish. IV. The isolation and structure of cannabinolic cannabidiolic and cannabigerolic acids. Tetrahedron 21: 1223-1229.

Miao V, Coëffet-Le Gal MF, Nguyen K, Brian P, Penn J, Whiting A, Steele J, Kau D, Martin S, Ford R, Gibson T, Bouchard M, Wrigley SK, Baltz RH (Mar. 2006). "Genetic engineering in Streptomyces roseosporus to produce hybrid lipopeptide antibiotics". Chemistry & Biology. 13 (3): 269-76.

Morales, P., D.P. Hurst & P.H. Reggio, (2017) Molecular Targets of the Phytocannabinoids: A Complex Picture. Prog Chem Org Nat Prod 103: 103-131.

Murdoch, D.R., G.R. Corey, B. Hoen, J.M. Miro, V.G. Fowler, Jr., A.S. Bayer, A.W. Karchmer, L. Olaison, P.A. Pappas, P. Moreillon, S.T. Chambers, V.H. Chu, V. Falco, D.J. Holland, P. Jones, J.L. Klein, N.J. Raymond, K.M. Read, M.F. Tripodi, R. Utili, A. Wang, C.W. Woods, C.H. Cabell & I. International Collaboration on Endocarditis-Prospective Cohort Study, (2009) Clinical presentation, etiology, and outcome of infective endocarditis in the 21st century: the International Collaboration on Endocarditis-Prospective Cohort Study. Arch Intern Med 169: 463-473.

Najafi K, Ganbarov K, Gholizadeh P, Tanomand A, Rezaee MA, Mahmood SS, Asgharzadeh M, Kafil HS. 2019. Oral cavity infection by Enterococcus faecalis: virulence factors and pathogenesis. Reviews in Medical Microbiology 29: OOO Publish Ahead of Print.

Nguyen KT, Kau D, Gu JQ, Brian P, Wrigley SK, Baltz RH, Miao V (Sep. 2006). "A glutamic acid 3-methyltransferase encoded by an accessory gene locus important for daptomycin biosynthesis in Streptomyces roseosporus". Molecular Microbiology. 61 (5): 1294-307.

Nguyen, K. T., He, X., Alexander, D. C., Li, C., Gu, J. Q., Mascio, C., Van Praagh, A., Mortin, L., Chu, M., Silverman, J. A., Brian, P., & Baltz, R. H. (2010). Genetically engineered lipopeptide antibiotics related to A54145 and daptomycin with improved properties. Antimicrobial agents and chemotherapy, 54(4), 1404-1413.

Odds, F.C., Synergy, antagonism, and what the chequerboard puts between them, Journal of Antimicrobial Chemotherapy, (2003) 52, 1.

Paganelli, Fernanda L et al. "Enterococcus faecium biofilm formation: identification of major autolysin AtlAEfm, associated Acm surface localization, and AtlAEfm-independent extracellular DNA Release." mBio vol. 4,2 e00154. Apr. 16, 2013, doi:10.1128/mBio.00154-13.

Prematunge, C., C. MacDougall, J. Johnstone, K. Adomako, F. Lam, J. Robertson & G. Garber, (2016) VRE and VSE Bacteremia Outcomes in the Era of Effective VRE Therapy: A Systematic Review and Meta-analysis. Infect Control Hosp Epidemiol 37: 26-35.

Russo, E.B., (2011) Taming THC: potential cannabis synergy and phytocannabinoid-terpenoid entourage effects. Br .1 Pharmacol 163:1344-1364.

Schleifer, K.H. & R. Kilpperbalz, (1984) Transfer of *Streptococcus-faecalis* and *Streptococcus-faecium* to the Genus *Enterococcus* Norn Rev as *Enterococcus-faecalis* Comb-Nov and *Enterococcus-faecium* Comb-Nov. Intl Syst Bacteriol 34: 31-34.

Steenackers, B.; De Cooman, L.; De Vos, D. (2015). "Chemical transformations of characteristic hop secondary metabolites in relation to beer properties and the brewing process: A review". Food Chemistry. 172: 742-756.

Trost and Dogra, (2007) Synthesis of (-)-Δ9-trans-Tetrahydrocannabinol—Stereocontrol via Mo-catalyzed Asymmetric Allylic Alkylation Reaction. Org Lett. Mar. 1, 2007; 9(5): 861-863.

Turner, C.E. & M.A. Eisohly, (1981) Biological activity of cannabichromene, its homologs and isomers. J Clin Pharmacol 21: 2835-2915.

Van Klingeren, B. & M. Ten Ham, (1976) Antibacterial activity of delta9-tetrahydrocannabinol and cannabidiol. Antonie Van Leeuwenhoek 42: 9-12.

Yu, V. L., T. P. Felegie, R. B. Yee, A. W. Pasculle, and F. H. Taylor. 1980. Synergistic interaction in vitro with use of three antibiotics simultaneously against Pseudomonas maltophilia. J. Infect. Dis. 142:602-607.

Zhong et al., (2017) Comparative genomic analysis of the genus *Enterococcus*. Microbiological Research, vol. 196, Mar. 2017, pp. 95-105.

Farha, et al.; "Uncovering the Hidden Antibiotic Potential of Cannabis"; ACS Infectious Diseases; vol. 6, No. 3, pp. 338-346 (Feb. 4, 2020).

Lang, et al.; "A reviewon recent research results (2008-2010) on essential oils as antimicrobials and antifungals. A review."; Flavour and Fragrance Journal; vol. 27, No. 1, pp. 13-39 (Aug. 16, 2011).

Schmidt, et al.; "Antimicrobial Activities of Single Aroma Compounds"; Natural Product Communications; vol. 5, No. 9, pp. 1365-1368 (Sep. 1, 2010).

* cited by examiner

ANTIBIOTIC CANNABINOID-TERPENE FORMULATIONS

CROSS-REFERENCE

This application is a continuation of U.S. Ser. No. 17/607,247, filed Oct. 28, 2021, which is a national stage filing under 35 U.S.C. § 371 of PCT/CA2020/050613, filed May 6, 2020, which claims the benefit of U.S. Provisional Patent Application No. 62/843,687, filed May 6, 2019, which applications are incorporated herein by reference in their entirety.

FIELD OF THE INVENTION

The invention is in the field of medicinal preparations comprising a mixture of two or more organic antibiotically active ingredients, optionally including specific phenolic cannabinoids in optional combination with specific sesquiterpenes in optional combination with a lipopeptide antibiotic such as daptomycin. The therapeutic use of cannabinoid and/or sesquiterpene formulations is also disclosed, for synergistic treatment of enterococcal infections, including combined uses with lipopeptide antibiotics such as daptomycin.

BACKGROUND OF THE INVENTION

*Enterococcus faecium* and *Enterococcus faecalis* are bacterial species that asymptomatically colonize the gastrointestinal (GI) tract in humans, but can also be pathogenic in certain circumstances (in the relevant literature, *Enterococcus faecium* was previously classified as *Streptococcus faecium*, see Schleifer & Kilpperbalz, 1984). In particular, these organisms are known to be a leading cause of dangerous infections in hospital patients being treated with antibiotics. During overgrowth, enterococci can penetrate the walls of the GI tract, moving into the liver or bloodstream where they can cause peritonitis, or systemic infections (bacteremia). Enterococci have been reported to be the third leading cause of endocarditis, the complication of blood infections that has the greatest risk of mortality (Murdoch et al., 2009). The intestinal colonization by enterococci, particularly in hospital patients, may facilitate continual person-to-person spread by environmental contamination from fecal droplets, leading to opportunistic infection. Passive transmission of fecal matter to the urinary tract in catheterized patients has reportedly made enterococci the second most common cause of catheter associated urinary tract infections (UTIs) which can result in kidney damage (Hidron et al., 2008). *E. faecalis* and *E. faecium* are associated with oral infections causing marginal periodontitis, root canal infections, primary endodontic infections, persistent/secondary infections, dental caries, peri-implantitis, periradicular abscesses and oral mucosal lesions (Najafi et al., 2019). *E. faecium* is also an important multidrug-resistant nosocomial pathogen causing biofilm-mediated infections in patients with medical devices (Paganelli et al., 2013).

Therapy for enterococcal infections is made more difficult by the frequency of antibiotic resistance. Traditional treatments involve penicillin administered with a synergistic aminoglycoside. However, the emergence of resistance, particularly mediated by a mutation in a penicillin binding protein (pbp5) in *E. faecium*, has severely limited the utility of this traditional strategy (Galloway-Pena et al., 2009, Arias & Murray, 2012). To combat penicillin resistant strains, vancomycin became the treatment of choice. However, *Enterococcus* spp. have become increasingly vancomycin resistant (VRE), frequently due to the acquisition of VanA and VanB vancomycin resistance systems (Arthur & Courvalin, 1993). From a public health perspective, the spread of VRE as a nosocomial infection has been particularly problematic since it reportedly causes 1.8 fold higher mortality and results in an average of 5 days longer hospital stay according to a meta-analysis (Prematunge et al., 2016).

Currently there are two drugs indicated for VRE treatment, linezolid and daptomycin. However, although linezolid resistance has been reported to be rare, daptomycin resistance appears to emerge frequently de novo during daptomycin treatment (Arias et al., 2011); in such strains, linezolid becomes the only effective antibiotic available. Linezolid as sole available therapy is problematic due to a litany of negative side effects, such as hepatic toxicity, myelosuppression, and serotonin syndrome (if used with other serotonergic drugs). Given the limited options for treatment of enterococcal infections and the adverse effects associated with existing treatments, new treatments are urgently needed.

A very wide range of physiological activities have been ascribed to compounds derived from flowering plants in the genus *Cannabis*, particularly phytocannabinoid compounds (see Cunha et al., 1980; Morales et al., 2017; U.S. Pat. No. 6,630,507). There are more than 80 cannabinoids found in cannabis plant extracts (Russo, 2011), including: cannabidiol (CBD), its acid form cannabidiolic acid (CBDA), cannabichromene (CBC), its acid form cannabichromic acid (CBCA), cannabigerol (CBG), its acidic form cannabigerolic acid (CBGA), tetrahydrocannabinol (THC), and its acidic form, tetrahydrocannabinolic acid (THCA). Studies have suggested that *Cannabis* extracts, or compounds derived from the *Cannabis* plant, have a very wide range of, often ill defined, anti-microbial activities (Van Klingeren & Ten Ham, 1976; Abdelaziz, 1982; Appendino et al., 2011; Appendino et al., 2008; Eisohly et al., 1982; Eisohly et al., 1982; Appendino et al., 2008; Turner & Eisohly, 1981; Mechoulam & Gaoni, 1965; WO2012/012498; WO2018/011813).

Terpenes are another molecular constituent of plants, including *Cannabis* plants, that have been attributed with a wide range of physiological activities. For example, the distinctive aroma and flavour that hops lends to beer reportedly comes in part from particular sesquiterpenes (including a-humulene and 13-caryophyllene; see Steenackers et al., 2015). The terpenes in *Cannabis* are reported to include well over 100 distinct compounds (Andre et al., 2016). It has been reported that aromatic terpenes may modulate the physiological effects of cannabinoids, particularly the psychoactive effects (Russo, 2011).

SUMMARY

Figures 1A, 1B, 1C:
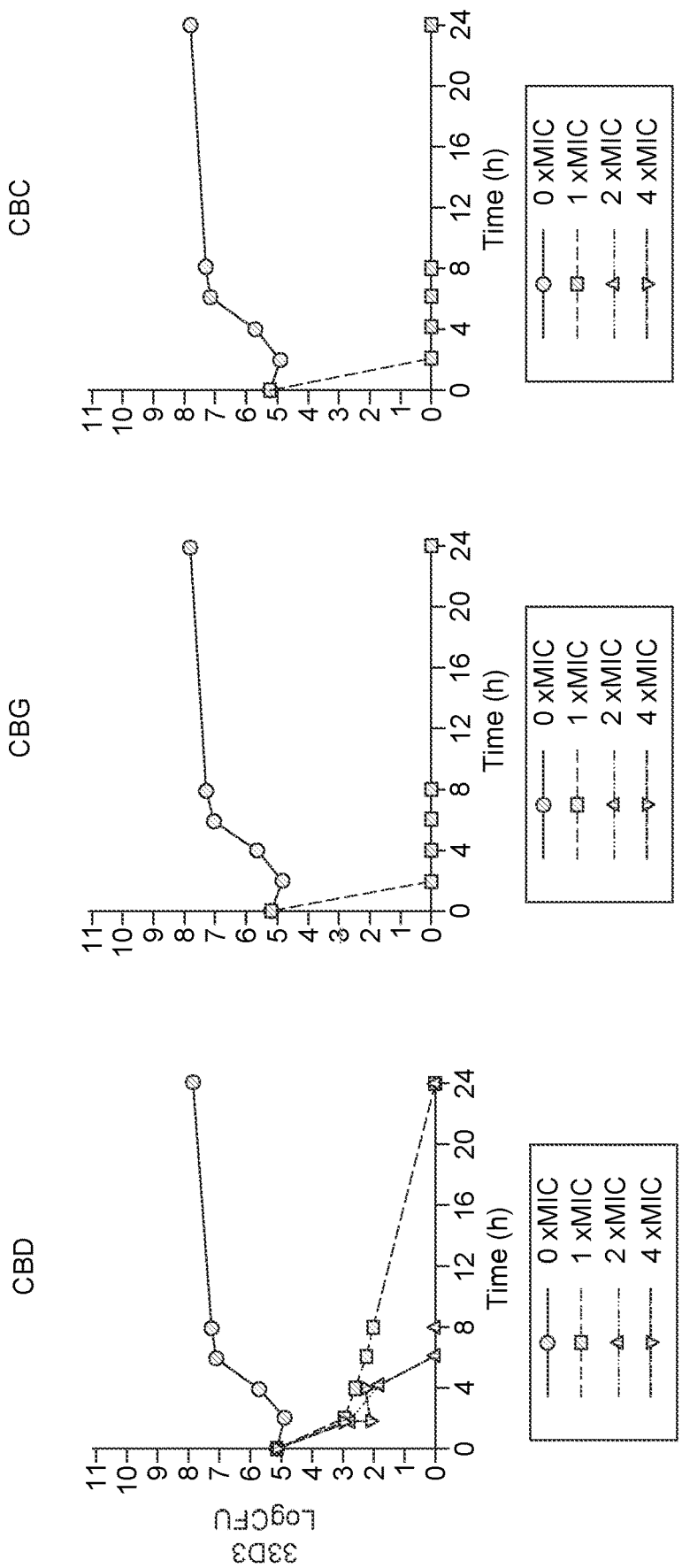
FIG. 1A-1L includes 12 line graphs, illustrating the effects of CBD, CBG or CBC on *E. faecium* viability. *Enterococcus* strains 3303 (A-C), 69C6 (D-F), 58C9 (G-I) and 55A6 (J-L) were incubated with Ox, 1× (1 mg/L), 2× (2 mg/L), or 4× (4 mg/L) the MIC of CBD (A,D,G,J), CBG (B,E,H,K) or CBC (C,F,I,L). CFU's were determined at 2, 4, 6, 8, and 24 h by serial dilution.
Figure 1D:
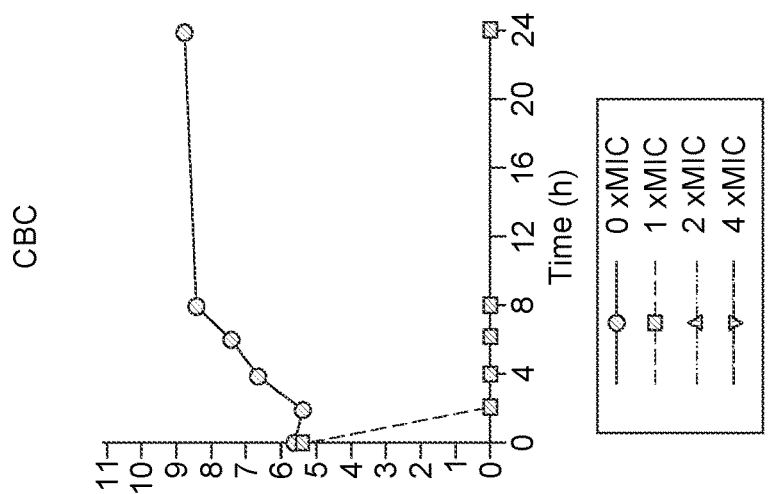
Figure 1E:
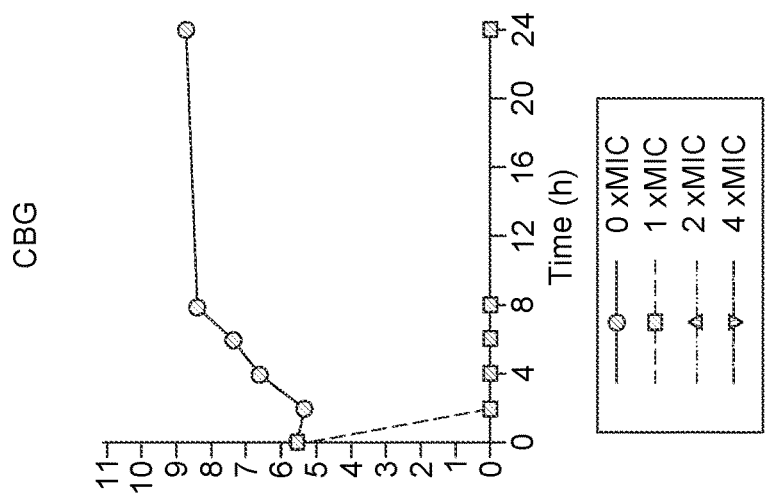
Figure 1F:
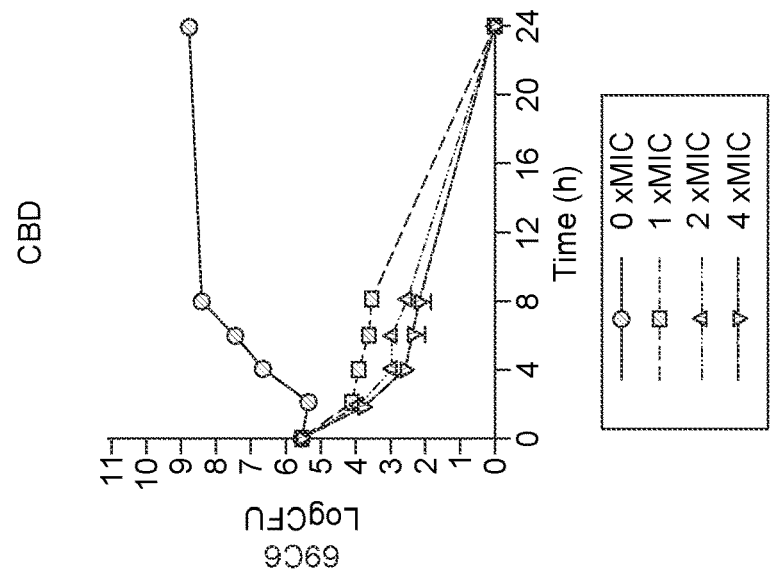
Figure 1I:
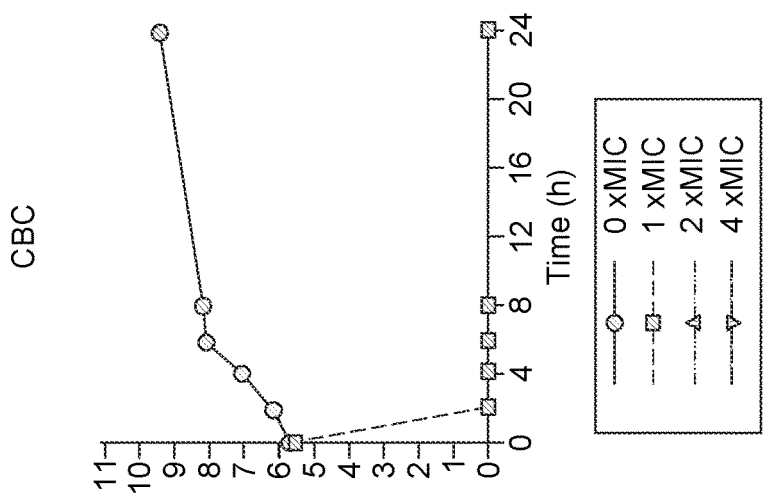
Figure 1H:
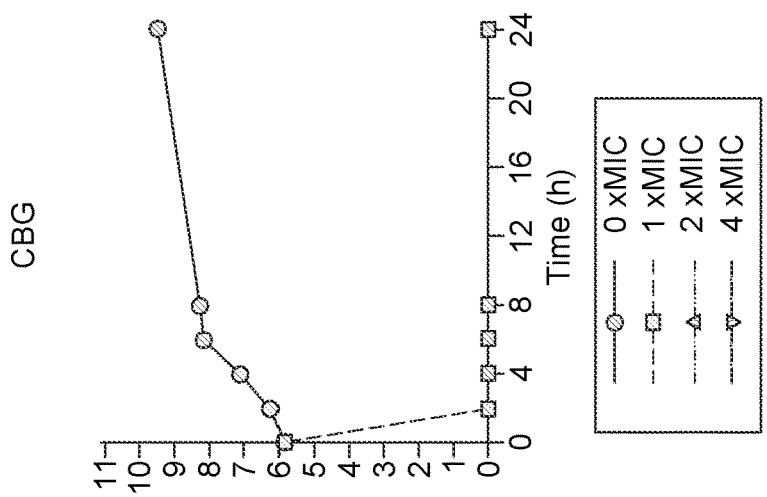
Figure 1G:
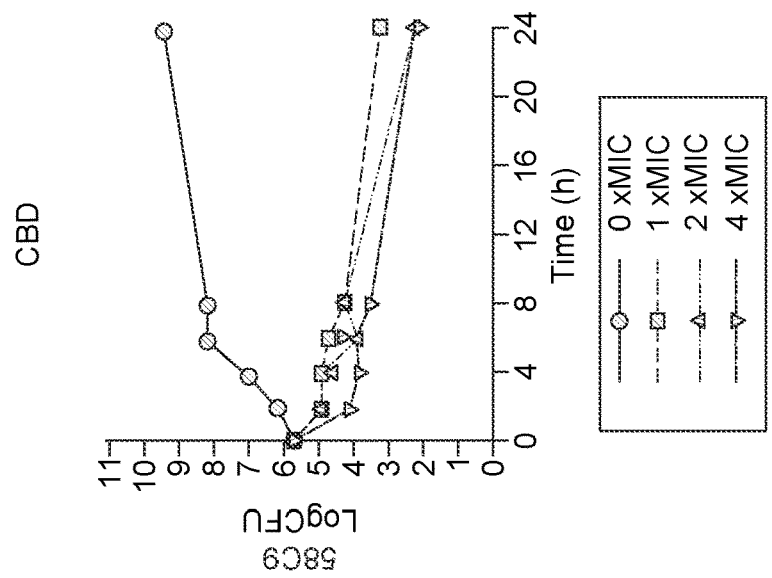
Figures 1J, 1K, 1L:
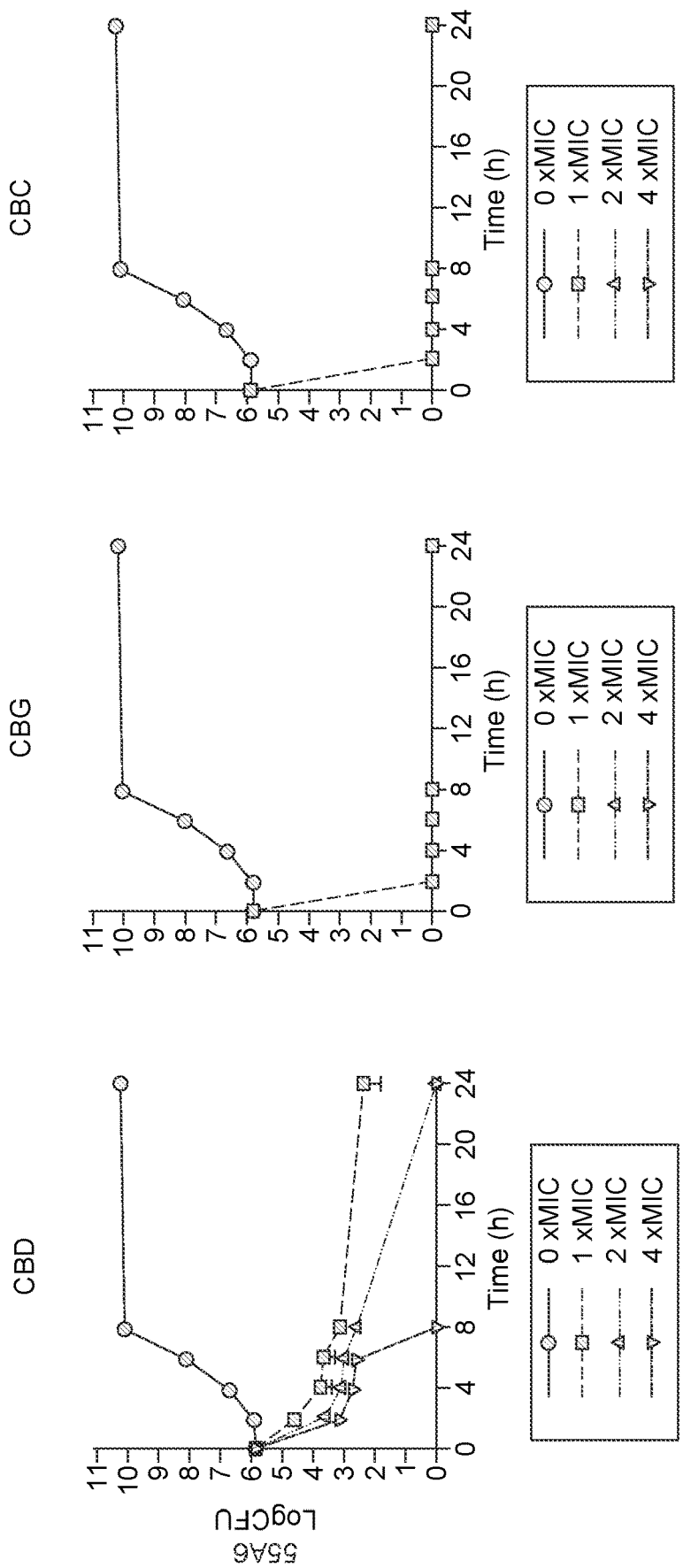

One general aspect of the innovations disclosed herein includes formulations that include at least two antibiotically active ingredients, for example selected from: a cannabinoid that is one or more of cannabichromene (CBC), cannabidiol (CBD) and/or cannabigerol (CBG). The formulations may also include a sesquiterpene that is one or both of a-humulene and/or 13-caryophyllene. The formulations can also include a lipopeptide antibiotic that is daptomycin or an analogue thereof. The formulations may include the antibiotically active ingredients in synergistically effective relative amounts, for example where an effective amount of the formulation is synergistically effective in an assay to inhibit growth and/or reproduction of an *Enterococcus faecium* or an *Enterococcus faecalis*.

Implementations may include one or more of the following features. The formulation where there are two antibiotically active ingredients, and the two antibiotically active ingredients are the cannabinoid and the sesquiterpene. The formulation where there are two antibiotically active ingredients, and the two antibiotically active ingredients are the cannabinoid and the lipopeptide antibiotic. The formulation including the cannabinoid, the sesquiterpene and the lipopeptide antibiotic. The formulation where there are two antibiotically active ingredients, and the two antibiotically active ingredients are the sesquiterpene and the lipopeptide antibiotic. The formulation of any one where the cannabinoid is one of CBC, CBD or CBG. The formulation of any one where the cannabinoid is two of CBC, CBD and CBG. The formulation of any one where the cannabinoid includes CBC, CBD and CBG. The formulation of any one where the sesquiterpene, if present, is one of a-humulene or 13-caryophyllene. The formulation of any one where the sesquiterpene, if present, includes a-humulene and 13-caryophyllene. The formulation of any one where the lipopeptide antibiotic, if present, is daptomycin. The formulation of any one where the sesquiterpene, when present, is present in a relative amount that provides at least a 2 to 128 fold decrease in the minimum inhibitory concentration (MIC) of the cannabinoid in the assay. The formulation of any one where the cannabinoid, when present, is present in a relative amount that provides at least a 2 to 128 fold decrease in the minimum inhibitory concentration (MIC) of the sesquiterpene in the assay. The formulation of any one where the sesquiterpene and/or the cannabinoid, when present, is present in a relative amount that provides at least a 2 to 128 fold decrease in the minimum inhibitory concentration (MIC) of the lipopeptide antibiotic in the assay. The formulation of any one where the molar ratio of the sesquiterpene to the cannabinoid, when present, is 50. The formulation of any one further including a pharmaceutically acceptable excipient, and where the antibiotically active ingredients are dissolved, dispersed, mixed or suspended in the formulation. The formulation of any one where the cannabinoid, when present, is present at 0.1-100 mg/L. The formulation of any one where the sesquiterpene, when present, is present at 0.1-500 mg/L. The formulation of any one where the cannabinoid and/or sesquiterpene, when present, are derived from a plant extract. The formulation where the plant is a *Cannabis sativa* or *Cannabis indica* plant. The formulation of any one where the formulation does not include any alternative cannabinoids, terpenes or lipopeptide antibiotics. The formulation of any one where the formulation includes essentially of two or more of the cannabinoid, the terpene or the lipopeptide antibiotic. Use of the formulation of any one to formulate a medicament. The use according where the medicament is for use in treating an enterococcal infection in a subject in need thereof. The use according where the enterococcal infection is an *Enterococcus faecium* or an *Enterococcus faecalis* infection. The use according to any one where the enterococcal infection is an oral infection. The use according where the oral infection is a marginal periodontitis, a root canal infection, a primary endodontic infection, a persistent or secondary infection, dental caries, peri-implantitis, periradicular abscess or an oral mucosal lesion. The use according to any one where the enterococcal infection is an antibiotic resistant enterococcal infection. The use according where the antibiotic resistant enterococcal infection is a vancomycin and/or daptomycin resistant enterococcal infection. The use according to any one where the formulation is for use in an amount that delivers an effective dose of the cannabinoid, when present, of from 1 to 5,000 mg per day, and/or an effective dose of the sesquiterpene, when present, of from 1 to 10,000 mg per day. Use of the formulation of any one to treat an enterococcal infection in a subject in need thereof. The formulation of any one for use to treat an enterococcal infection in a subject in need thereof. The formulation where the enterococcal infection is an *Enterococcus faecium* or an *Enterococcus faecalis* infection. The formulation where the enterococcal infection is an oral infection. The formulation where the oral infection is a marginal periodontitis, a root canal infection, a primary endodontic infection, a persistent or secondary infection, dental caries, peri-implantitis, periradicular abscess or an oral mucosal lesion. The formulation of any one where the enterococcal infection is an antibiotic resistant enterococcal infection. The formulation where the antibiotic resistant enterococcal infection is a vancomycin and/or daptomycin resistant enterococcal infection. The formulation of any one where the formulation is for use in an amount of that delivers an effective dose of the cannabinoid, when present, of from 1 to 5,000 mg per day, and/or an effective dose of the sesquiterpene, when present, of from 1 to 10,000 mg per day.

Alternative aspects of the disclosed innovations include methods of treating an enterococcal infection in a subject in need thereof, including administering to the subject an effective amount of the formulations disclosed herein. Implementations may include one or more of the following features. The method including two antibiotically active ingredients, where the two antibiotically active ingredients are the cannabinoid and the sesquiterpene, further including treating the subject with an effective amount of one or more antibiotics, optionally where the antibiotic is daptomycin. The method including administering the cannabinoid in an effective amount of 1-5,000 mg/day. The method of any one including administering the sesquiterpene in an effective amount of 1-10,000 mg/day. The method of any one where the subject is a mammal. The method where the mammal is a human.

Alternative aspects of the present innovations include methods of treating a microbial infection in a subject in need thereof, including administering to the subject, sequentially or in combination, an effective amount of at least two antibiotically active compounds selected from: a cannabinoid that is one or more of cannabichromene (CBC), cannabidiol (CBD) and/or cannabigerol (CBG). The method of treating also includes a sesquiterpene that is one or both of a-humulene and/or 13-caryophyllene; and. The method of treating also includes a lipopeptide antibiotic that is daptomycin or an analogue thereof. The method of treating also includes where the antibiotically active compounds are administered in synergistically effective relative amounts effective to treat the microbial infection.

Implementations of the disclosed methods may include one or more of the following features. The method where the synergistically effective relative amounts are synergistically effective to inhibit growth and/or reproduction of an *Enterococcus faecium* or an *Enterococcus faecalis* in an assay. The method where the cannabinoid and the sesquiterpene are co-administered, or the sesquiterpene and the lipopeptide antibiotic are co-administered, or the cannabinoid and the lipopeptide antibiotic are co-administered, or the cannabinoid the sesquiterpene and the lipopeptide antibiotic are co-administered. The method where the cannabinoid and the sesquiterpene, or the sesquiterpene and the lipopeptide antibiotic, or the cannabinoid and the lipopeptide antibiotic, or the cannabinoid the sesquiterpene and the lipopeptide antibiotic, are administered sequentially, in any order. The method of any one further including further treating the subject with the lipopeptide antibiotic alone. The method of any one where the cannabinoid, if administered, is one of CBC, CBD or CBG. The method of any one where the cannabinoid, if administered, is two of CBC, CBD and CBG. The method of any one where the cannabinoid, if administered, includes CBC, CBD and CBG. The method of any one where the sesquiterpene, if administered, is one of a-humulene or 13-caryophyllene. The method of any one where the sesquiterpene, if administered, includes a-humulene and 13-caryophyllene. The method of any one where the lipopeptide antibiotic, if administered, is daptomycin. The method of any one where the sesquiterpene, if administered, is administered in a relative amount that provides at least a 2 to 128 fold decrease in the minimum inhibitory concentration (MIC) of the cannabinoid when administered. The method of any one where the cannabinoid, if administered, is administered in a relative amount that provides at least a 2 to 128 fold decrease in the minimum inhibitory concentration (MIC) of the sesquiterpene when administered. The method of any one where the sesquiterpene and/or the cannabinoid, when administered, is administered in a relative amount that provides at least a 2 to 128 fold decrease in the minimum inhibitory concentration (MIC) of the lipopeptide antibiotic when administered. The method of any one where the microbial infection is an enterococcal infection. The method where the enterococcal infection is an *Enterococcus faecium* or an *Enterococcus faecalis* infection. The method where the enterococcal infection is an oral infection. The method where the oral infection is a marginal periodontitis, a root canal infection, a primary endodontic infection, a persistent or secondary infection, dental caries, peri-implantitis, periradicular abscess or an oral mucosal lesion. The method of any one where the microbial infection is an antibiotic resistant infection. The method where the antibiotic resistant infection is a vancomycin and/or daptomycin resistant microbial infection.

In an alternative aspect, methods are provided for treating a bacterial infection in a subject in need thereof, comprising administering to the subject an effective amount of: a cannabinoid that is one or more of cannabichromene (CBC), cannabidiol (CBD) and/or cannabigerol (CBG); and, a lipopeptide antibiotic that is daptomycin or an analogue thereof; wherein the cannabinoid and the lipopeptide antibiotic are administered in an antibiotically effective weight ratio of from 16:1 to 1:16; and, wherein: if the cannabinoid is CBD, then the lipopeptide antibiotic is administered in an effective amount that is less than 4 mg/kg; and/or, if the cannabinoid is CBD, then the bacterial infection comprises infection by an infectious organism having a daptomycin MIC of 4 µg/ml or greater; and/or, if the cannabinoid is CBD, then the bacterial infection comprises infection by an infectious organism for which results from an assay of bacterial growth indicate that daptomycin produces an inhibitory and/or bactericidal effect at concentrations of less than 4 µg/ml when administered with CBD in an amount that is less than the MIC of CBD. The infection may for example include an infection by an *Enterococcus faecium* or an *Enterococcus faecalis*. These treatments may further include administering to the subject an effective amount of a sesquiterpene that is one or both of a-humulene and/or 13-caryophyllene.

In an alternative aspect, antibiotic formulations are provided that include: a cannabinoid that is one or more of cannabichromene (CBC) and/or cannabigerol (CBG); and, a lipopeptide antibiotic that is daptomycin or an analogue thereof; wherein the cannabinoid and the lipopeptide antibiotic are present in an antibiotically effective weight ratio of from 16:1 to 1:16. The cannabinoid may for example be present in an amount that reduces the minimum inhibitory concentration (MIC) of the lipopeptide antibiotic in an antibiotic assay, such as an Enterococcal assay that assesses the inhibition of growth and/or reproduction of an *Enterococcus faecium* or an *Enterococcus faecalis*. In select embodiments, the cannabinoid reduces the MIC of the lipopeptide antibiotic in the assay when the cannabinoid is present in an amount that is less than the MIC of the cannabinoid. These formulations may further include a sesquiterpene, such as one or both of a-humulene and/or 13-caryophyllene.

DETAILED DESCRIPTION OF THE INVENTION

In one aspect, pharmaceutical formulations are provided that include at least two antibiotically active ingredients, selected from: a cannabinoid that is one or more of cannabichromene (CBC), cannabidiol (CBD) and/or cannabigerol (CBG); a sesquiterpene that is one or both of a-humulene and/or 13-caryophyllene; and, a lipopeptide antibiotic that is daptomycin or an analogue thereof. The antibiotically effective ingredients may be provided in synergistically effective relative amounts. For example, the cannabinoid and the sesquiterpene may be provided at concentrations that are only antibiotically active in synergistic combinations, such as ::::1 µg/ml cannabinoid and ::::32 µg/ml terpene. In synergistic combination, the inhibitory concentrations of the partners may for example decrease, for example by two or more fold, for example from 2-16 fold. Alternatively, the relative weight ratio of cannabinoid to sesquiterpene may for example be from about 1:5 to 1:50, or 1:8 to 1:32, or from 1:12 to 1:32. The relative concentration of the antibiotically active ingredients in the formulation may be arranged so that an effective amount of the formulation would be synergistically effective in an assay to inhibit growth and/or reproduction of an *Enterococcus faecium* or an *Enterococcus faecalis*. A formulation that provides this synergistic formulation may be used for treating enterococcal or other microbial infections, for example for treating infections of enterococcal species that are relatively closely related to a reference strain of *Enterococcus faecium* or *Enterococcus faecalis* (see Zhong et al., 2017). For example, enterococcal species amenable to treatment may be at least as closely related to the reference strain as are the most distantly related strains of *E. faecium* and *E. faecalis*. The microorganisms amenable to treatment may for example be resistant to antibiotics, for example VRE strains or strains resistant to daptomycin. *Enterococcus durans* is for example amenable to treatment, for example in the context of veterinary diseases. Other enterococcal species closely related to *E. faecium* or *E. faecalis* may for example include *E. mundtii, E. durans, E. hirae, E. ratti, E. vilforum, E. thailandicus* and *E. phoeniculicola, E. termitis, E. quebecensis, E. moraviensis, E. caccae, E. haemoperoxidus* and *E. silesiacus*]

In select embodiments, synergies and/or potentiation effects are maximized using concentrations of antibiotically active components that are below the MICs for each component, for example just below the MICs. The components may accordingly be present in relative amounts that approximate the ratio of the respective MICs for the components. For example, this may occur when the molar ratio terpene/cannabinoid is 50 (reflecting the MIC ratio of the components).

The molar ratio of cannabinoid to sesquiterpene may for example be between 1:100 and 50:1. For example, synergistic combinations may have a molar ratio of cannabinoid to sesquiterpene between 1:8 and 1:32. A pharmaceutically acceptable excipient may optionally be included in the formulation, and the cannabinoid and sesquiterpene may be dissolved, dispersed, mixed or suspended in the formulation. One method of formulation may involve producing a sterile lyophilized powder, for example in a vial for reconstitution.

The cannabinoid and sesquiterpene may for example be obtained from a plant extract, such as an extract of *Cannabis sativa* or *Cannabis indica*. Biosynthetic approaches to the production of cannabinoids and sesquiterpenes are also available, as are a variety of synthetic approaches (based for example on approaches used to synthesize THC/dronabinol, see U.S. Pat. No. 7,323,576 and Trost and Dogra, 2007). Alternative approaches involve expressing cannabinoid biosynthetic genes in recombinant hosts, such as recombinant yeast (see Luo et al., 2019).

Derivatives or analogues of daptomycin may for example be used as lipopeptide antibiotics, as alternatives or in addition to use of daptomycin itself (see Nguyen et al., 2006; Baltz, 2006; and, Miao et al., 2006; Nguyen et al., 2010). In select embodiments, a daptomycin analogue is a lipopeptide antibiotic that has an antibiotic activity that synergizes with one or more of the cannabinoids and/or sesquiterpenes in the formulations disclosed herein, for example in assay of antibiotic activity against enterococcal species. Daptomycin analogues or derivatives may for example differ from daptomycin by virtue of the substitution of one or more amino acids therein, such as by conservative substitutions, for example substitutions of 1, 2, 3, 4 or 5 amino acids therein, for example substitutions with natural or non-natural amino acids. Daptomycin analogues may for example include cyclic lipodepsipeptide daptomycin, or derivatives thereof in which the fatty acid chain attached to the Trp' amino group is an anteiso-undecanoyl, iso-dodecanoyl or anteiso-tridecanoyl group.

One or more additional compounds may be included, or specifically excluded, in alternative formulations, including for example: terpenes, terpenoids, sterols, triglycerides, alkanes, squalene, tocopherol, carotenoids, chlorophyll, flavonoid glycosides, or alkaloids.

Anti-microbial formulations may be used to prophylactically or therapeutically treat microbial infections, or otherwise inhibit microbial growth or multiplication. An antibiotic is an antimicrobial that is active against bacteria, and in this context includes naturally-occurring and synthetic substances that kill or inhibit the growth or multiplication of bacteria by any mechanism, including antiseptic or disinfectant modalities.

Subjects amenable to treatment include mammalian subjects, such as human patients, laboratory animals (e.g., primates, rats, mice), livestock (e.g., cows, sheep, goats, pigs, horses, fowl), or household pets (e.g., dogs, cats, rodents, birds), for example belonging to the taxonomic groups of primates, canines, felines, bovines, caprines, equines, ovines, porcines, rodents, Ayes or lagomorphs. Human patients to be treated may for example be male or female, or at a specific stage of development: neonate, infant, juvenile, adolescent, adult and geriatric. Specific veterinary indications amenable to treatment may for example include enterococcal infections in poultry, for example treatment of *Enterococcus cecorum* infections in chickens.

In alternative embodiments, formulation may be administered in a dosage or dosage form that delivers and/or sustains synergistically effective amounts of the active ingredients.

The cannabinoid and/or sesquiterpene components of the formulation may for example be in the form of a plant extract, or be derived from a plant extract, or be obtained from a culture, such as a culture of a recombinant host, such as a recombinant yeast expressing the components. Humulene and 13-caryophyllene are isomers, often found together in a variety of plants. In addition, a pharmaceutically acceptable excipient may be included, and the formulation may be provided in a titratable dosage form. In select embodiments, the cannabinoid components of the formulation may be obtained as an extract from a plant of the *Cannabis* genus, for example *Cannabis sativa* or *Cannabis indica*, or from a culture of recombinant yeast hosts. A wide variety of methods may be used to prepare these plant extracts, including, but not limited to, supercritical or subcritical extraction with $CO_2$, extraction with hot gas, and extraction with solvents. Formulations may also specifically exclude additional terpenoids or terpenes, including plant-derived terpenoids or terpenes, such as astaxanthin or other sesquiterpenes, tetraterpenes, triterpenes, diterpenes or monoterpenes.

A titratable dosage may for example be adapted to allow a patient to take the medication in doses smaller than the unit dose, wherein a "unit dose" is defined as the maximum dose of medication that can be taken at any one time or within a specific dosage period. Titration of doses will allow different patients to incrementally increase the dose until they feel that the medication is efficacious, as not all patients will require the same dose to achieve the same benefits. A person with a larger build or faster metabolism may require larger doses to achieve the same effect as another with a smaller build or slower metabolism. Therefore, a titratable dosage has advantages over a standard dosage form.

In select embodiments, formulations may be adapted to be delivered in such a way as to target one or more of the following: sublingual, buccal, oral, rectal, nasal, parenteral and via the pulmonary system. Formulations may for example be in one or more of the following forms: gel, gel spray, tablet, liquid, capsule, by injection, or for vaporization.

Conventional pharmaceutical practice may be employed to provide suitable formulations or compositions to administer the formulations to subjects. Routes of administration may for example include, parenteral, intravenous, intradermal, subcutaneous, intramuscular, intracranial, intraorbital, ophthalmic, intraventricular, intracapsular, intraspinal, intrathecal, intracisternal, intraperitoneal, intranasal, inhalational, aerosol, topical, sublingual or oral administration. Therapeutic formulations may be in the form of liquid solutions or suspensions; for oral administration, formulations may be in the form of tablets or capsules; for intranasal formulations, in the form of powders, nasal drops, or aerosols; and for sublingual formulations, in the form of drops, aerosols or tablets.

Methods well known in the art for making formulations are found in, for example, "Remington: The Science and Practice of Pharmacy" (21st edition), ed. David Troy, 2006, Lippincott Williams & Wilkins. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Pharmaceutical compositions of the present invention may be in any form which allows for the composition to be administered to a patient. For example, the composition may be in the form of a solid, liquid or gas (aerosol). Pharmaceutical composition of the invention are formulated so as to allow the active ingredients contained therein to be bioavailable upon administration of the composition to a patient. Compositions that will be administered to a patient may take the form of one or more dosage units, where for example, a tablet, capsule or cachet may be a single dosage unit, and a container of the compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a formulation of the present invention as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid formulation for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent. When the composition is in the form of a capsule, e.g., a gelatin capsule, it may contain, in addition to materials of the above type, a liquid carrier such as polyethylene glycol or a fatty oil.

The formulation may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydoxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical formulations of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

The pharmaceutical formulation may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The formulation may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the aminocyclohexyl ether compound is dispersed homogeneously therein by stirring. The molten homogeneous mixture is then poured into convenient sized molds, allowed to cool and thereby solidify.

The formulation may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The pharmaceutical formulation may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit.

Some biologically active compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

The present invention also provides kits that contain a pharmaceutical formulation, together with instructions for the use of the formulation. Preferably, a commercial package will contain one or more unit doses of the formulation. Formulations which are light and/or air sensitive may require special packaging and/or formulation. For example, packaging may be used which is opaque to light, and/or sealed from contact with ambient air, and/or formulated with suitable coatings or excipients.

The formulations of the invention can be provided alone or in combination with other compounds (for example, small molecules, nucleic acid molecules, peptides, or peptide analogues), in the presence of a carrier or any pharmaceutically or biologically acceptable carrier. As used herein "pharmaceutically acceptable carrier" or "excipient" includes any and all solvents, dispersion media, coatings, antibacterial and antifungal agents, isotonic and absorption delaying agents, and the like that are physiologically compatible. The carrier can be suitable for any appropriate form of administration. Pharmaceutically acceptable carriers generally include sterile aqueous solutions or dispersions and sterile powders. Supplementary active compounds can also be incorporated into the formulations.

An "effective amount" of a formulation according to the invention includes a therapeutically effective amount or a prophylactically effective amount. A "therapeutically effective amount" refers to an amount effective, at dosages and for periods of time necessary, to achieve the desired therapeutic result. A therapeutically effective amount of a formulation may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the formulation or active compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to or at an earlier stage of disease, so that a prophylactically effective amount may be less than a therapeutically effective amount. For any particular subject, the timing and dose of treatments may be adjusted over time (e.g., timing may be daily, every other day, weekly, monthly) according to the individual need and the professional judgment of the person administering or supervising the administration of the compositions.

With respect to effective amounts of antibiotic treatments, although the daptomycin susceptibility breakpoint for enterococci is considered to be 4 mg/L, ongoing debate exists as to whether this is appropriate given that approved doses are optimized only when MIC::::1 mg/L. For example, a recent study found that when the MIC was 4 mg/L, the probability of attaining target pharmacokinetic parameters in daptomycin-treated enterococcal bacteremia reached only 1.5-5.5% when 6 mg/kg doses were administered (Avery, Lindsay M et al. "Pharmacodynamic Analysis of Daptomycin-treated Enterococcal Bacteremia: It Is Time to Change the Breakpoint." Clinical Infectious Diseases Vol. 68, 10 (2019): 1650-1657).

In therapeutic applications, synergy between active ingredients occurs when an observed combined therapeutic effect is greater than the sum of therapeutic effects of individual active ingredients, or a new therapeutic effect is produced that the active ingredients could not produce alone. Accordingly, when components of a formulation are present in synergistically effective amounts, the formulation yields a therapeutic effect that is greater than would be achieved by the individual active ingredients administered alone at comparable dosages. In this context, the enhancement of therapeutic effect may take the form of increased efficacy or potency and/or decreased adverse effects. The synergistic effect may be mediated in whole or in part by the pharmacokinetics and/or pharmacodynamics of the active ingredients in a subject, so that the amount and proportion of the ingredients in the formulation may be synergistic in vivo. This in vivo synergy may be effected with a formulation that includes the active ingredients in amounts and proportions that are also synergistic in in vitro assays of efficacy. As used herein, the term "synergistically effective amounts" accordingly refers to amounts that are synergistic in vivo and/or in vitro. A numeric quantification of synergy is often expressed as a fractional inhibitory concentration index (FICI), which represents the sum of the fractional inhibitory concentrations (FICs) of each drug tested, where the FIC is determined for each drug by dividing the minimum inhibitory concentration (MIC, the lowest concentration of the drug which prevents visible growth of the bacterium in a standard in vitro assay-standard colorometric assay based on resazurin) of each drug when used in combination by the MIC of each drug when used alone. In very general terms, a FICI lower or higher than 1 indicates positively correlated activity (at least additive or potentiation) or an absence of positive interactions, respectively. More definitively, synergy of two compounds may be conservatively defined as a FICI of ::::0.5 (see Odds, 2003; with additivity or potentiation corresponding to a FICI of >0.5 to ::::0.75; no interaction (indifference) corresponding to a FICI of >1 to ::::4; and antagonism corresponding to a FICI of >>4). Synergy of three compounds has been defined as a FICI of ::::1.0. (Berenbaum, 1978; Yu et al., 1980). To estimate the optimal concentrations in triple combinations, the optimal concentrations of trans-caryophyllene and cannabinoid were utilized in combination with a series of daptomycin dilutions.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention. Any priority document(s) and all publications, including but not limited to patents and patent applications, cited in this specification are incorporated herein by reference. All documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual publication were specifically and individually indicated to be incorporated by reference herein and as though fully set forth herein. The invention includes all embodiments and variations substantially as hereinbefore described and with reference to the examples and drawings. In some embodiments, the invention excludes steps that involve medical or surgical treatment.

EXAMPLES

Example 1

As illustrated in this Example, the non-psychotropic cannabinoids, cannabidiol, cannabigerol and cannabichromene (i.e., CBD, CBG, and CBC), have bacteriostatic (Tables 1, 2) and bactericidal (FIG. 1) activities against *E. faecium* and *E. faecalis*, including strains that are sensitive or resistant to vancomycin and, in some cases, also resistant to daptomycin. At equal concentrations of CBD, CBG, or CBC, the kinetics of *E. faecium* killing with CBG and CBC are faster than for CBO (FIG. 1). It is further shown that cannabinoids can also increase the activity of daptomycin (MIC) by 8-128 fold (Table 3). In addition, we demonstrate that each cannabinoid has species specific activities against Gram positive (but not Gram negative) bacteria (Table 1).

As further illustrated in this Example, the non-psychotropic cannabinoids, cannabidiol, cannabigerol and cannabichromene (i.e., CBO, CBG, and CBC), trans-caryophyllene, and daptomycin act in synergy. Assays for interactions between all pairwise as well as triple combinations of cannabinoids (CBC, CBO, CBG), trans caryophyllene, and daptomycin are shown in Table 4. All pairwise combinations showed synergistic (FICI:::: 0.5) or potentiating (FICI 0.5, ::::0.75) interactions. However, while a-humulene (13-caryophyllene, data not shown) and trans caryophyllene had synergistic activities with CBC, CBO, or CBG (Table 4), other terpenes (a-pinene and R-(+) limonene) had no detectable activity either alone or in combination (MIC>32 mg/L; data not shown). All triple combination were synergistic (FICIs<1.0). Under these conditions, the MIC of daptomycin decreased 256-fold (from 8 to 0.03 µg/ml in the presence of CBO and trans caryophyllene; Table 5) or >512 fold (from >16 to 0.03 in the presence of CBC and trans caryophyllene, Table 70).

As illustrated in Tables 6 and 7, analyses of double and triple combinations against the drug resistant (daptomycin and vancomycin) strain VRE 55A6 showed that daptomycin/terpene/cannabinoid combinations are even more effective against this strain (compared to the vancomycin/daptomycin sensitive strain 3303), increasing the MIC of daptomycin >500 fold (effectively suppressing the daptomycin resistance phenotype).

The data presented in this Example was obtained as set out below.

MIC Determination for all Bacteria Except *Mycobacterium* Species:

Pre-cultures of bacteria growing in their corresponding liquid media (defined below) were diluted to an 00600 of 0.0025 and 100 µl was added to 100 µl of medium containing serial 2-fold dilutions of cannabinoid (cannabinoid stocks in methanol or acetonitrile for acidic forms, were diluted in growth medium) in 96-well plates. Plates were then incubated for 20-24 h at 37° C., and growth was recorded as 00600 in a Thermo Scientific™ Varioskan™ Flash Multimode Reader.

MIC Determination for *Mycobacterium abscessus* ATCC 19977:

Pre-cultures growing in MHII medium with 0.05% tyloxapol were diluted to an 00600 of 0.005 in MHII medium, and 100 µl was added to 100 µl of MHII medium containing serial 2-fold dilutions of cannabinoid (cannabinoid stocks in methanol or acetonitrile for acidic forms were diluted in growth medium) in 96-well plates. Plates were then incubated for 48 h, followed by the addition of 30 µl the colorimetric reagent resazurin in water (10 mg/100 ml). Plates were incubated for an additional 24 h, and growth was recorded as conversion of culture color from blue to pink.

MIC Determination for *Mycobacterium tuberculosis* H37Rv:

Pre-cultures of *M. tuberculosis* growing in 7H9 medium plus 0.05% tyloxapol, were grown to mid-log phase and diluted to 00600 0.0025 in the same medium without tyloxapol. 50 µL of diluted culture were used to inoculate wells in 96-well plates containing 50 µL of the same medium with serial 2-fold dilutions of cannabinoid (cannabinoid stocks in methanol or acetonitrile were diluted in growth medium). Plates were incubated for 5 days at 37° C., 5% CO2, followed by the addition of 10 µL PrestoBlue Cell Viability Reagent to each well. Plates were incubated for a further 24 hat 37° C., 5% CO2 and then fluorescence (excitation 530 nm, emission 590 nm) was read on a Synergy HT plate reader.

Growth Media Used for Various Organisms:
   *Enterococcus faecium*: all strains (clinical isolates 33D3, 69C6, 58C9, and 55A6), MHII (Mueller Hinton II)
   *Enterococcus faecalis*: MHII (Mueller Hinton II)
   *Streptococcus pyogenes* ATCC 51878: BHI (Brain Heart Infusion*)
   *Staphylococcus aureus* MRSA USA 300: LB (Luria-Bertani)
   *Staphylococcus epidermidis* ATCC 14990: NB (Nutrient Broth)
   *Staphylococcus epidermidis* ATCC 12228: NB (Nutrient Broth)
   *Mycobacterium abscessus* ATCC 19977: MHII (Mueller Hinton II)
   *Mycobacterium tuberculosis* H37Rv: 7H9
   *Mycobacterium tuberculosis* H37Rv: PB (Proskauer and Beck+glucose and sodium pyruvate)
   *Acinetobacter baumanii* ATCC 19606: NB (Nutrient Broth)
   *Escherichia coli* HB101: (LB (Luria-Bertani)
   *Pseudomonas aeruginosa* ATCC 27853: Tryptic Soy Broth
      *Streptococcus pyogenes* ATCC 51878 was grown at 37° C. in a tri-gas incubator.

Method for FIG. 1.

Pre-cultures were diluted to an OD600 of 0.0025 in 3 ml MHII medium supplemented with appropriate concentrations of cannabinoids. At various time points, 100 µl of culture was removed from each tube and serial 10-fold dilutions were spotted onto MHII agar plates (10 µl), which were incubated at 37° C. for 24 h, and the colonies were counted (CFU).

Method for Tables 1-3. MIC Determinations were Carried Out as Described Above.

Method for Tables 4-7. Interaction of Cannabinoids CBC, CBD and CBG with Terpenes and Daptomycin:

FICI values was determined in a 96 well checkerboard format using the MIC assay for cannabinoids (compound A), terpenes (compound B), and daptomycin (compound C) alone and in combinations. Terpene stocks were prepared in DMSO and diluted in the growth medium. The fractional inhibitory concentration for each compound was calculated as follows: FICA=(MIC of compound A in the presence of compound B)/(MIC of compound A alone). Similarly, the FICs for compounds B and C were calculated. The FICI was calculated as FICA plus FICs plus FICc.

TABLE 1

Table 1: Cannabinoids have activity against diverse Gram-positive bacteria but not against Gram-negative bacteria, (*Pseudomonas aeruginosa* ATCC 27853, *Acinetobacter baumanii* ATCC 19606, *E. coli* HB101, data not shown). Sensitivities are expressed as MICs (mg/L).

| | CBD | CBDA | CBG | CBGA | CBC | CBCA |
|---|---|---|---|---|---|---|
| *Staphylococcus aureus* MRSA | 2 | 16 | 1 | 1 | 4 | 4 |

TABLE 1-continued

Table 1: Cannabinoids have activity against diverse Gram-positive bacteria but not against Gram-negative bacteria, (*Pseudomonas aeruginosa* ATCC 27853, *Acinetobacter baumanii* ATCC 19606, *E. coli* HB101, data not shown). Sensitivities are expressed as MICs (mg/L).

| | CBD | CBDA | CBG | CBGA | CBC | CBCA |
|---|---|---|---|---|---|---|
| *Streptococcus pyogenes* ATCC 51878 | 1 | 8 | 1 | 2 | 1 | 0.5-1 |
| *Enterococcus faecium* 33D3 | 1-2 | 16 | 1-2 | 16 | 1-2 | 4 |
| *Enterococcus faecalis* | 2 | 16 | 1 | 8 | 2 | 4 |
| *Staphylococcus epidermidis* ATCC 14990 | 2 | 4 | 1-2 | 2 | 4 | 2 |
| *Staphylococcus epidermidis* ATCC 12228 | 2 | 4 | 2 | 2 | 4 | 2 |
| *Mycobacterium abscessus* ATCC 19977 | 16 | 32 | 2 | 16 | 4 | 4 |
| *Mycobacterium tuberculosis* H37Rv Media PB | 4 | 4 | 2 | 2 | 4 | 4 |
| *Mycobacterium tuberculosis* H37Rv Media 7H9 | 16 | 2 | 2 | 4 | 8 | 2 |

TABLE 2

Cannabinoid activity against clinical enterococcal strains (vancomycin sensitive, vancomycin resistant, and resistant to both vancomycin and daptomycin), expressed as MICs (mg/L).

| Cannabinoids | 3303 | 69C6* | 58C9*# | 55A6*# |
|---|---|---|---|---|
| CBD | 1 | 1 | 1 | 2 |
| CBDA | 16 | 16 | 16 | 16 |
| CBG | 1 | 1 | 1 | 1 |
| CBGA | 16 | 8 | 16 | 8 |
| CBC | 1 | 1 | 1 | 1 |
| CBCA | 4 | 4 | 4 | 2 |
| Daptomycin | 2 | 1 | 8 | 8 |

*Vancomycin resistant
0aptomycin resistant (MIC is greater that 4 mg/L)

TABLE 3

Cannabinoids potentiate the activity of daptomycin against clinical isolates of *E. faecium*.

| | Fold reduction in daptomycin MIC in combination with: | | |
|---|---|---|---|
| Isolate | CB0 | CBG | CBC |
| 3303 | 16 | 32 | 128 |
| 69C6* | 4 | 4 | 32 |
| 55a6*# | 16 | 4 | 512 |
| 58c9*# | 32 | 64 | 8 |

*indicates that the strain is vancomycin resistant.
0aptomycin resistant strains (MIC is greater than 4 mg/L).

TABLE 4

Synergistic and potentiating interactions of pairwise
and triple combinations of Cannabinoids (CBC,
CBD, or CBG), Trans-caryophyllene, and Daptomycin
inhibit *E. faecium* 3303 growth.

A Pairwise interactions of CBC, Trans-caryophyllene and Daptomycin

| Combination | FICI | Interaction |
|---|---|---|
| Daptomycin CBC | 0.51 | Synergy |
| Daptomycin Trans-caryophyllene | 0.25-0.75 | Potentiation/Synergy |
| CBC Trans-caryophyllene | 0.31 | Synergy |

4B. Pairwise interactions of CBD, Trans-caryophyllene and Daptomycin

| Combinations | FICI | Interaction |
|---|---|---|
| Daptomycin CBD | 0.56 | Likely Synergy |
| Daptomycin Trans-caryophyllene | 0.25-0.75 | Potentiation/Synergy |
| CBD Trans-caryophyllene | 0.37 | Synergy |

4C. Pairwise interactions of CBG, Trans-caryophyllene and Daptomycin

| Combinations | FICI | Interaction |
|---|---|---|
| Daptomycin CBG | 0.53 | Synergy |
| Daptomycin Trans-caryophyllene | 0.25-0.75 | Potentiation/Synergy |
| CBG Trans-caryophyllene | 0.37-0.5 | Synergy |

4D. Interactions of Triple Combinations of a cannabinoid (CBC, CBD, or CBG), Trans-caryophyllene and Daptomycin

| Combinations | FICI | Interaction |
|---|---|---|
| Daptomycin CBC, Trans-caryophyllene | 0.75* | Synergy |
| Daptomycin CBD, Trans-caryophyllene | 0.75 | Synergy |
| Daptomycin CBG, Trans-caryophyllene | 0.81 | Synergy |

*For triple combinations, FICI <1.0 represents synergy

TABLE 5

Maximal fold increases in the activities of individual Cannabinoids
(CBC, CBD, CBG), Trans-caryophyllene and Daptomycin in pairwise
and triple combinations against *E. faecium* 3303.

5A. Pairwise interactions of CBC, Trans-caryophyllene and Daptomycin

| Combinations | MIC (mg/L) Alone | MIC (mg/L) In combination | Max. fold change In MIC |
|---|---|---|---|
| Daptomycin | 4 | 0.03125 | 128↑ |
| CBC | 2 | 0.5 | 4↑ |
| Daptomycin | 4 | 0.5 | 8↑ |
| Trans-caryophyllene | >16 | 4 | >4↑ |
| CBC | 2 | 0.125 | 16↑ |
| Trans-caryophyllene | 16 | 0.25 | 64↑ |

5B. Pairwise interactions of CBD, Trans-caryophyllene and Daptomycin

| Combination | MIC (mg/L) Alone | MIC (mg/L) In combination | Max. fold change in MIC |
|---|---|---|---|
| Daptomycin | 4 | 0.25 | 16↑ |
| CBD | 4 | 1 | 4↑ |
| Daptomycin | 4 | 0.5 | 8↑ |
| Trans-caryophyllene | >16 | 4 | >4↑ |
| CBD | 2 | 0.125 | 16↑ |
| Trans-caryophyllene | 16 | 2 | |

5C. Pairwise interactions of CBG, Trans-caryophyllene and Daptomycin

| Combination | MIC (mg/L) Alone | MIC (mg/L) In combination | Max. fold change in MIC |
|---|---|---|---|
| Daptomycin | 8 | 0.25 | 32↑ |
| CBG | 4 | 0.125 | 32↑ |
| Daptomycin | 4 | 0.5 | 8↑ |
| Trans-caryophyllene | >16 | 4 | >4↑ |
| CBG | 2 | 0.125 | 16↑ |
| Trans-caryophyllene | 32 | 4 | 8↑ |

5D. Interactions of Triple Combinations of a Cannabinoid (CBC, CBD, or CBG), Trans-caryophyllene and Daptomycin

| Combinations | MIC (mg/L) Alone | MIC (mg/L) In combination | Max. fold change in MIC |
|---|---|---|---|
| Daptomycin | 8 | 4 | 2↑ |
| CBC, Trans-caryophyllene | 2, 16 | 0.25, 2 | 8↑ |
| Daptomycin | 8 | 0.03 | 256↑ |
| CBD, Trans-caryophyllene | 2, 16 | 0.5, 2 | 4, 8↑ |
| Daptomycin | 8 | 2 | 4↑ |
| CBG, Trans-caryophyllene | 1, 16 | 0.25, 1 | 4, 16↑ |

TABLE 6

Synergistic and potentiating pairwise or triple interactions
of cannabinoids (CBC, CBD, CBG), trans-caryophyllene, and
daptomycin inhibit *E. faecium* VRE 55A6 growth.

6A. Pairwise interactions of CBC, Trans-caryophyllene and Daptomycin

| Combinations | FICI | Interaction |
|---|---|---|
| Daptomycin CBC | 0.5 | Synergy |
| Daptomycin Trans-caryophyllene | 0.5-0.625 | Synergy/Potentiation |
| CBC Trans-caryophyllene | 0.51-0.53 | Synergy |

6B. Pairwise interactions of CBD, Trans-caryophyllene and Daptomycin

| Combinations | FICI | Interaction |
|---|---|---|
| Daptomycin CBD | 0.5 | Synergy |
| Daptomycin Trans-caryophyllene | 0.5-0.625 | Synergy/Potentiation |
| CBD Trans-caryophyllene | 0.5-0.75 | Potentiation |

TABLE 6-continued

Synergistic and potentiating pairwise or triple interactions of cannabinoids (CBC, CBD, CBG), trans-caryophyllene, and daptomycin inhibit *E. faecium* VRE 55A6 growth.

6C. Pairwise interactions of CBG, Trans-caryophyllene and Daptomycin

| Combinations | FICI | Interaction |
|---|---|---|
| Daptomycin CBG | 0.75 | Potentiation |
| Daptomycin Trans-caryophyllene | 0.5-0.625 | Synergy/Potentiation |
| CBG Trans-caryophyllene | >1 | No interaction |

60. Interactions of Triple Combinations of a Cannabinoid (CBC, CBD, or CBG), Trans-caryophyllene and Daptomycin

| Combinations | FICI | Interaction |
|---|---|---|
| Daptomycin CBC, Trans-caryophyllene | 0.25-0.56 | Synergy |
| Daptomycin CBD, Trans-caryophyllene | 0.25-0.44 | Synergy |
| Daptomycin CBG, Trans-caryophyllene | 0.5-0.69 | Synergy |

* For triple combinations, FICI <1.0 represents synergy

TABLE 7

Maximal fold increases in the activities of individual cannabinoids (CBC, CBD, CBG), trans-caryophyllene and daptomycin in pairwise or triple combinations against *E. faecium* VRE 55A6.

7A Pairwise interactions of CBC, Trans-caryophyllene and Daptomycin

| | MIC (mg/L) | | Max. fold |
|---|---|---|---|
| Combinations | Alone | In combination | change in MIC |
| Daptomycin | 16 | 0.031 | 512 |
| CBC | 2 | 0.25 | 8 |
| Daptomycin | 16 | 8 | 2 |
| Trans-caryophyllene | >16 | 2 | >8 |
| CBC | 1 | 0.5 | 2 |
| Trans-caryophyllene | >32 | 1 | >32 |

7B. Pairwise interactions of CBD, Trans-caryophyllene and Daptomycin

| | MIC (mg/L) | | Max. fold |
|---|---|---|---|
| Combinations | Alone | In combination | change in MIC |
| Daptomycin | 16 | 1 | 16 |
| CBD | 4 | 0.5 | 8 |
| Daptomycin | 16 | 8 | 2 |
| Trans-caryophyllene | >16 | 2 | >8 |
| CBD | 2 | 1 | 2 |
| Trans-caryophyllene | >32 | 8 | >4 |

7C. Pairwise interactions of CBG, Trans-caryophyllene and Daptomycin

| | MIC (mg/L) | | Max. fold |
|---|---|---|---|
| Combinations | Alone | In combination | change in MIC |
| Daptomycin | 16 | 4 | 4 |
| CBG | 4 | 2 | 2 |
| Daptomycin | 16 | 8 | 2 |
| Trans-caryophyllene | >16 | 2 | >8 |
| CBG | 2 | 2 | none |
| Trans-caryophyllene | >32 | >32 | none |

TABLE 7-continued

Maximal fold increases in the activities of individual cannabinoids (CBC, CBD, CBG), trans-caryophyllene and daptomycin in pairwise or triple combinations against *E. faecium* VRE 55A6.

70. Interactions of Triple Combinations of a Cannabinoid (CBC, CBD, or CBG), Trans-caryophyllene and Daptomycin

| | MIC (mg/L) | | Max. fold |
|---|---|---|---|
| Combinations | Alone | In combination | change in MIC |
| Daptomycin | >16 | 0.03 | >512 |
| CBC, Trans-caryophyllene | 2, >64 | 0.25, 2 | 8, >32 |
| Daptomycin | >16 | 2 | >8 |
| CBD, Trans-caryophyllene | 4, >64 | 0.5, 2 | 8, >32 |
| Daptomycin | >16 | 2 | >8 |
| CBG, Trans-caryophyllene | 2, >64 | 0.5, 2 | 4, >32 |

The foregoing data illustrate particularly important interactions with certain cannabinoid-daptomycin combinations, evidencing synergy: e.g. Table 6A FICI=0.5 for CBC+Daptomycin; Table 6B FICI=0.5 for CBD+daptomycin. In addition to the respective relative amounts that gave synergy, this data illustrates that other relative amounts produce surprising and unexpected significant growth inhibition of *E. faecium*: e.g. Table 5A shows a 128-fold reduction in the MIC of daptomycin (MIC reduced to from 4 to 0.03125 mg/L). This effect occurred when CBC was present at ½ its MIC (i.e., CBC MIC reduced from 1 to 0.5 mg/L; data not shown). This interaction occurred with each partner in potentiating ratios, relative amounts of 0.5:0.03125=16:1 CBC:Daptomycin.

Example 2: Cannabinoid Sensitization to Daptomycin

Figure 2:
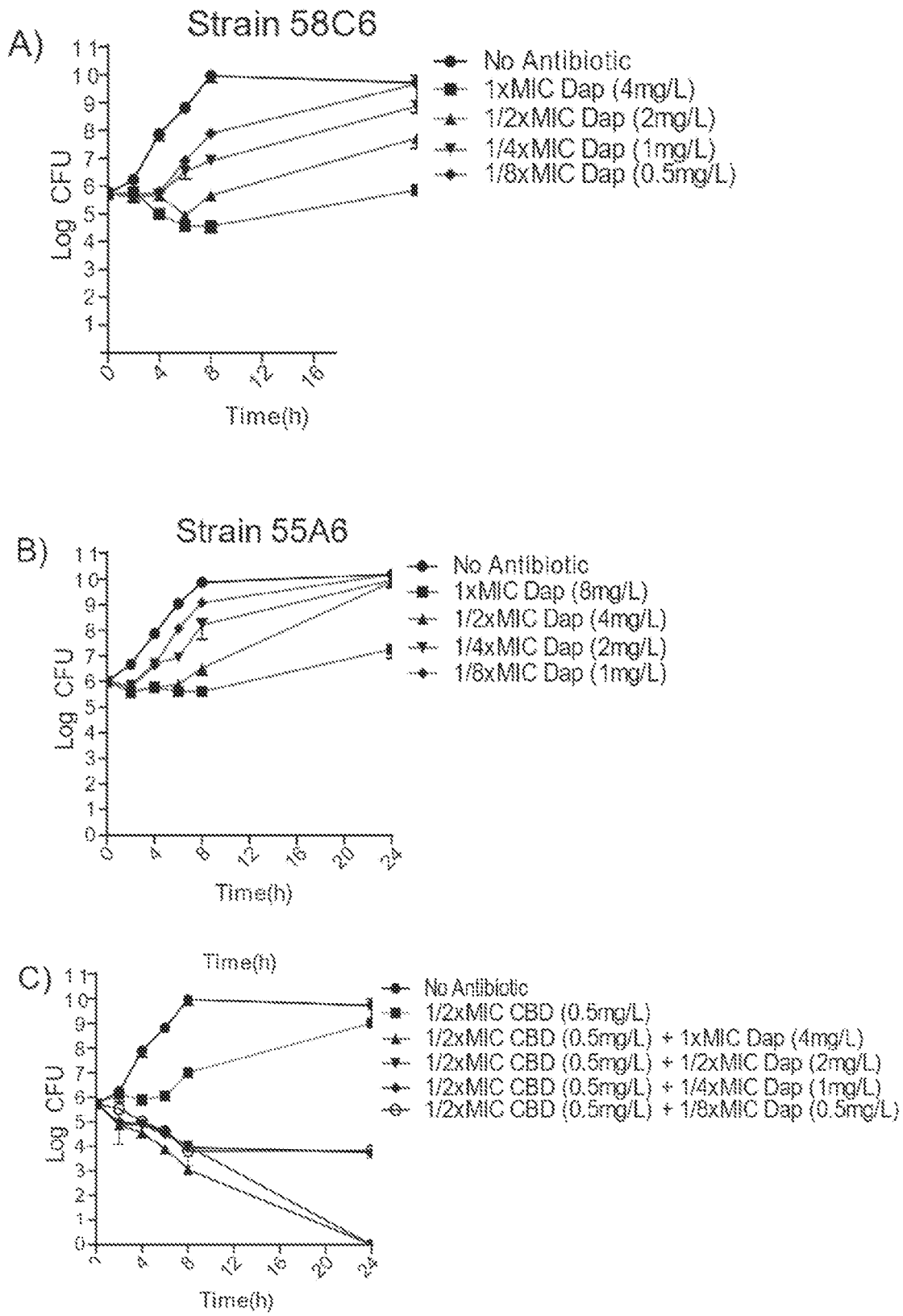
FIG. 2 includes 8 line graphs, illustrating the effects of daptomycin (Dap), and Dap in combination with CBD, CBG or CBC, on daptomycin resistant *E. faecium* VRE strains 58C9 and 55A6 (*E. faecium* clinical strain 55A6 is resistant to daptomycin with a daptomycin MIC=8 mg/L). As illustrated, adding approximately ½ MIC of each cannabinoid facilitated killing by daptomycin at approximately ¼-⅛× the MIC of daptomycin.
Figure 2:
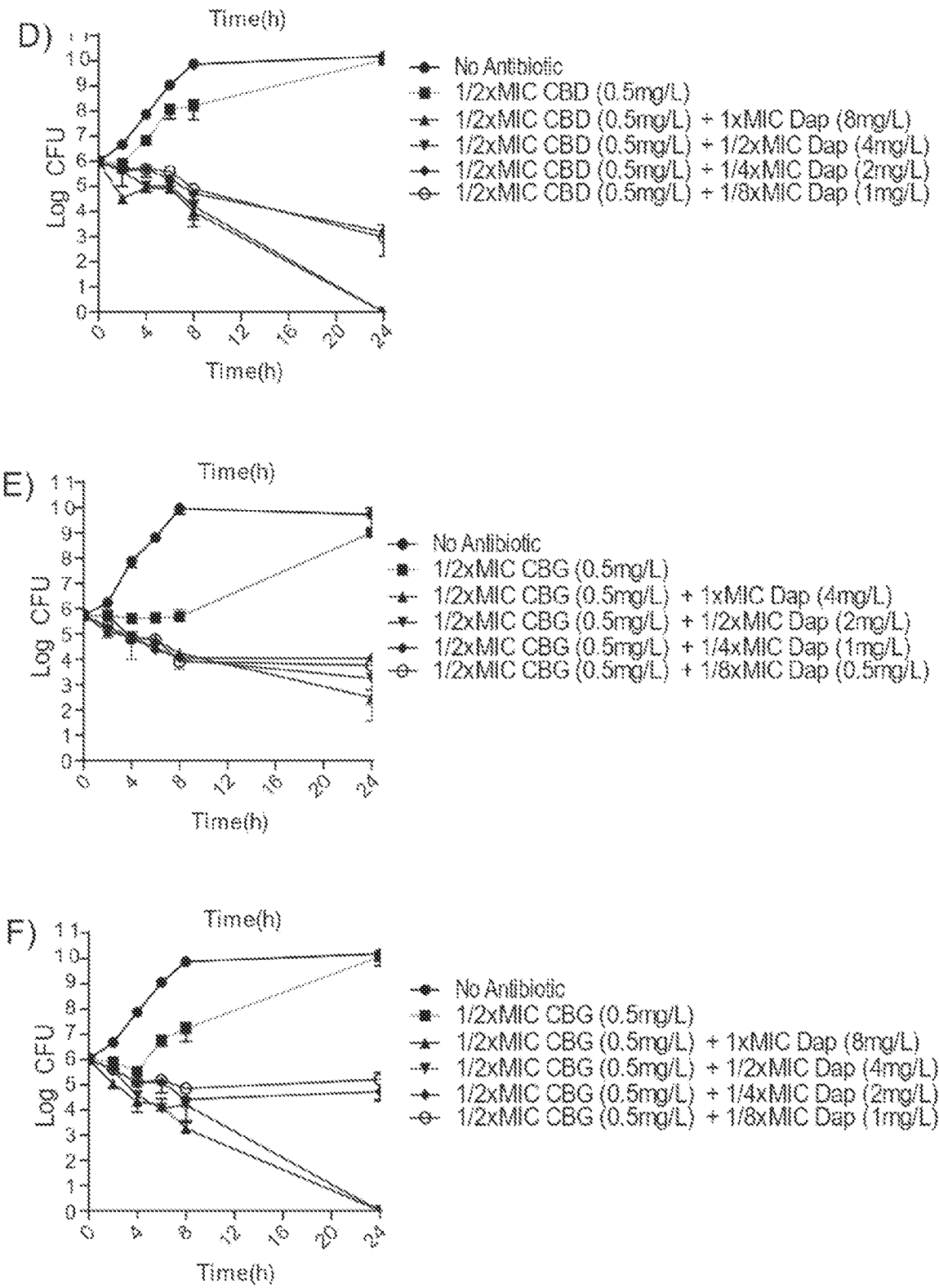
Figure 2:
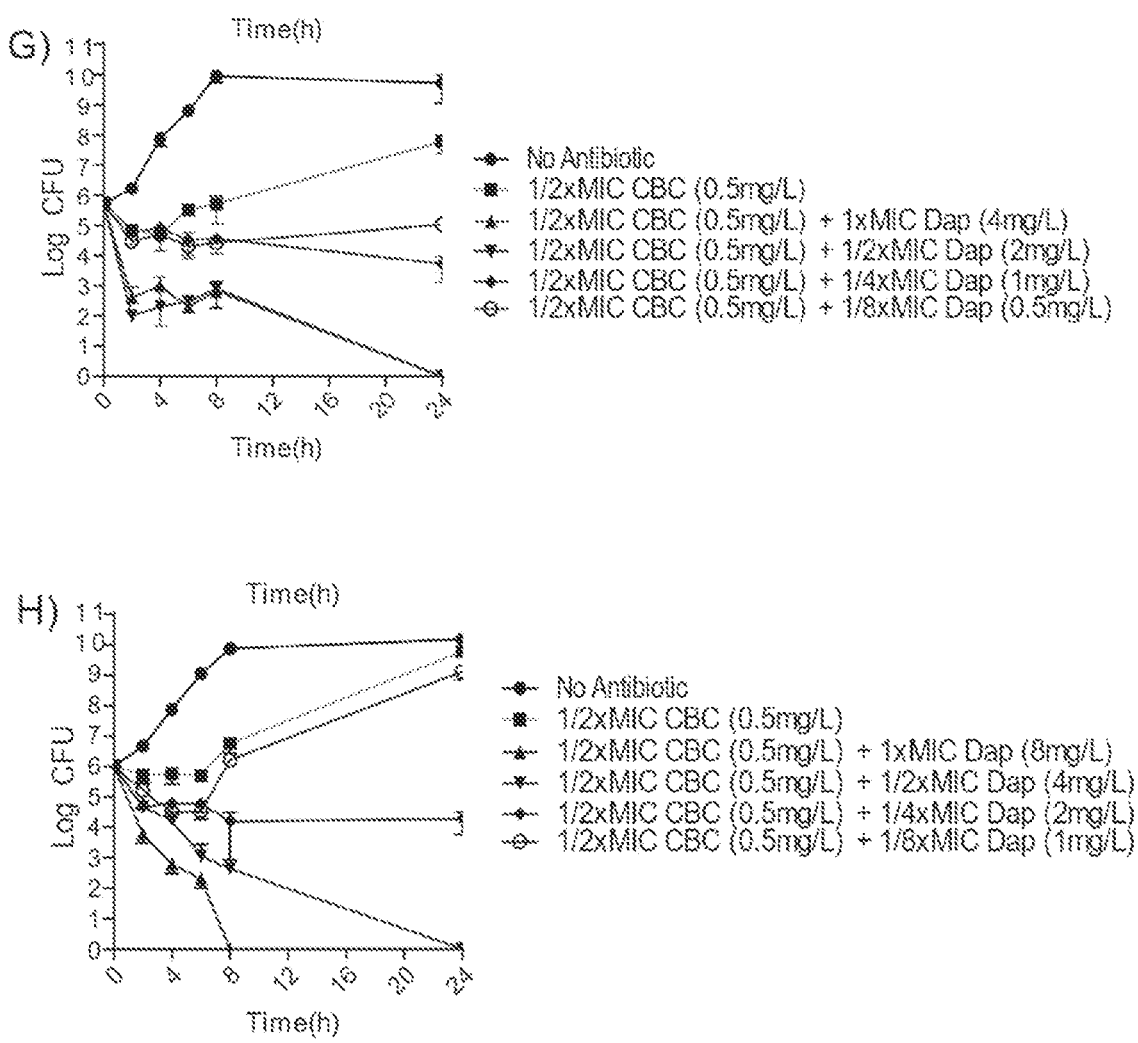

As illustrated in FIG. 2, cannabinoids sensitize antibiotic resistant Enterococcal strains to daptomycin. FIG. 2 reflects data illustrating the effects of daptomycin (Dap), and Dap in combination with CBD, CBG or CBC, on daptomycin resistant *E. faecium* VRE strains 58C9 and 55A6. *E. faecium* strain 55A6 is resistant to daptomycin with a daptomycin MIC=8 mg/L. *E. faecium* strains 58C9 and 55A6 were incubated with no cannabinoid (A,B), or ½× (0.5 mg/L) MIC of CBD (C,D), CBG (E,F) or CBC (G,H) with 1× (4 mg/L for 58C9; 8 mg/L for 55A6), ½× (2 mg/L for 58C9; 4 mg/L for 55A6), ¼× (1 mg/L for 58C9; 2 mg/L for 55A6) or ⅛× (0.5 mg/L for 58C9; 1 mg/L for 55A6) MIC of daptomycin. Aliquots were removed at 2, 4, 6, 8 and 24 h for CFU enumeration. Data points are the means from three replicates with standard deviations presented as error bars. As illustrated, adding approximately ½ MIC of each cannabinoid facilitated killing by daptomycin at ¼-1/Sx the MIC of daptomycin.

Figure 3:
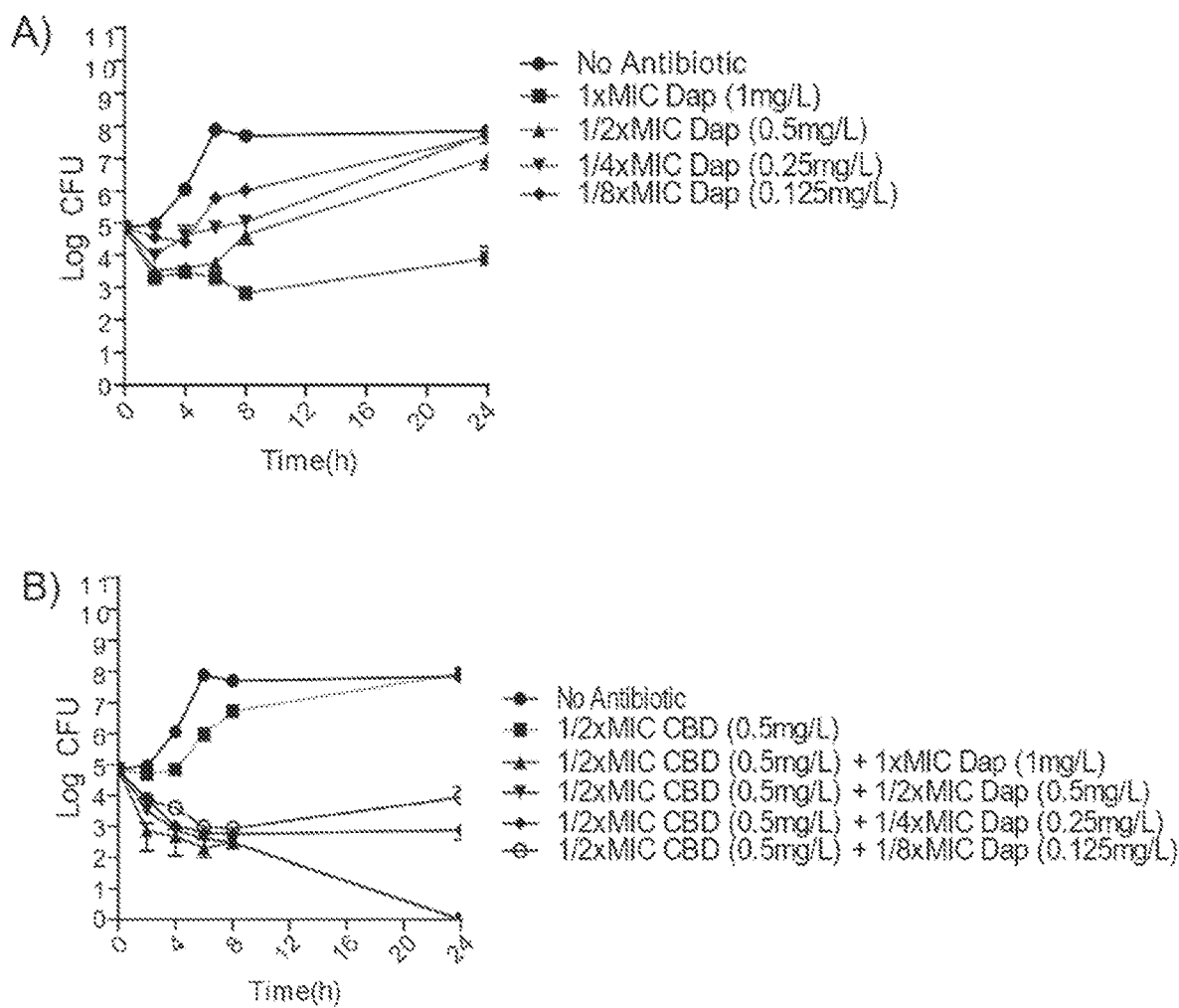
FIG. 3 includes 4 line graphs, illustrating the effect of various concentrations of CBD, CBG and CBC on bactericidal activity of daptomycin. *E. faecium* strain 3303 was incubated with (A) no cannabinoid, or ½× (0.5 mg/L) MIC of (B) CBD, (C) CBG) or (D) CBC with 1× (1 mg/L), ½× (0.5 mg/L), ¼× (0.25 mg/L) or ⅛× (0.125 mg/L) MIC of daptomycin. Aliquots were removed at 2, 4, 6, 8 and 24 h plated to monitor viability (CFU). Data points are the means from three replicates with standard deviations presented as error bars.
Figure 3:
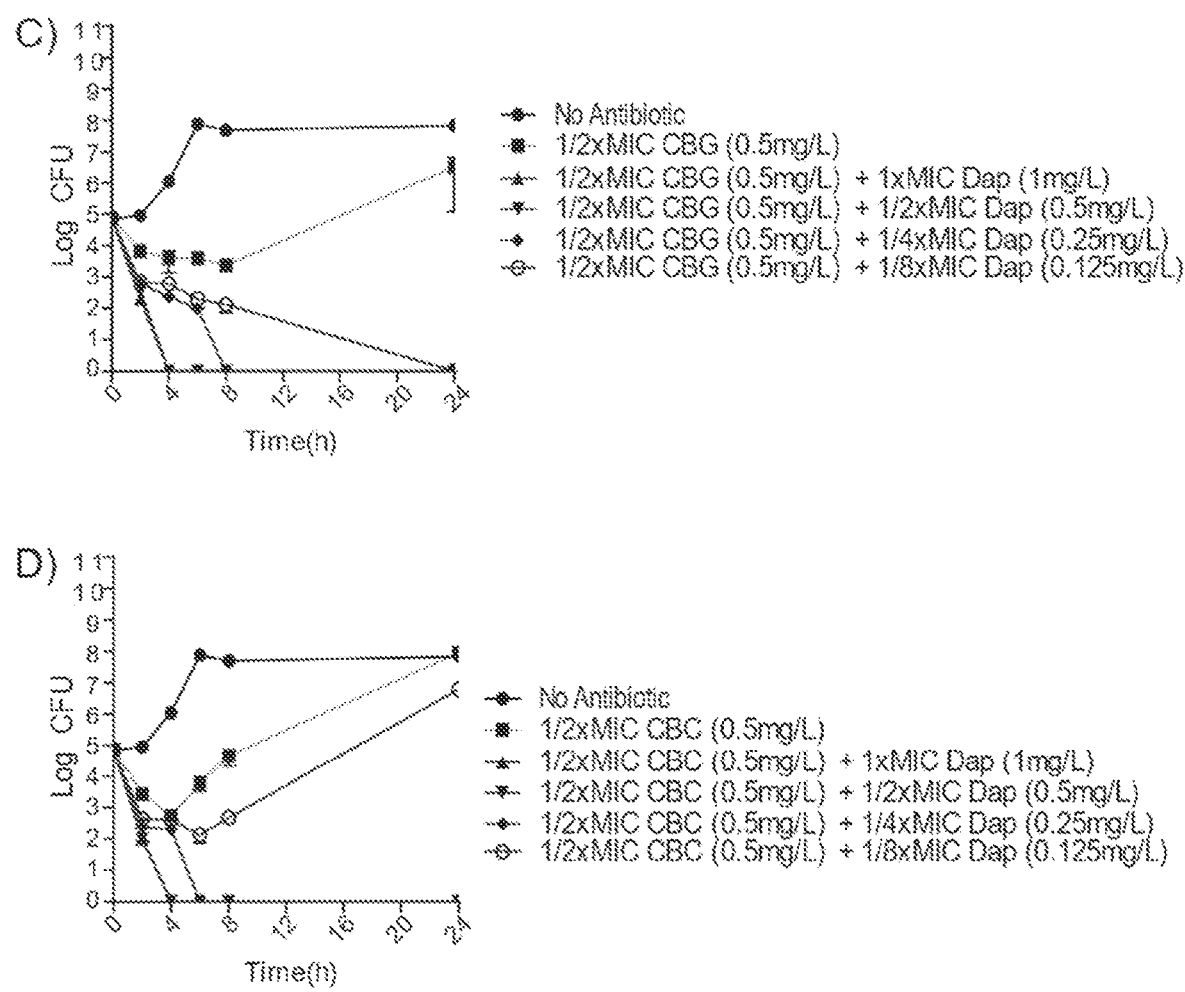

To further illustrate the bactericidal potentiation activity of CBD, CBG and CBC with daptomycin, kill curves were generated with *E. faecium* strain 3303 (daptomycin sensitive, MIC=1), as illustrated in FIG. 3. This data is usefully compared to the data in FIG. 2 for *E. faecium* strains 58C9 (daptomycin intermediate resistance MIC=4) and 55A6 (daptomycin resistant, MIC=8). As illustrated, strains were each incubated with ⅛× to 1×MIC of daptomycin (0.25-1 mg/L daptomycin for 3303, 0.5-4 mg/L daptomycin for 58C9 and 1-8 mg/L daptomycin for 55A6) and with 0.5× MIC of CBO, CBG or CBC. At ½×MIC there was effectively no inhibition of growth by a cannabinoid or daptomycin in all strains. Of note, although daptomycin did inhibit growth at 1×MIC, there was no reduction in CFU. However, ½×MIC of CBO, CBG or CBC in combination of 1×-⅛×MIC of daptomycin significantly inhibited growth of all strains and reduced CFU, thereby demonstrating bactericidal activity (FIGS. 2 and 3). This has particularly important clinical relevance, since daptomycin is generally not used to treat patients infected by strains classified as daptomycin resistant (MIC>4 mg/L). Strains 58C9 and 55A6 are daptomycin intermediate resistant and resistant respectively, but in the presence of ½×MIC of CBO, CBG or CBC, as little as 1 mg/L Oaptomycin (⅛×MIC) could significantly reduce the CFU at 24 h (FIG. 2).

This Example further illustrates that a broad range of relative cannabinoid-daptomycin amounts can provide surprising and unexpected results, as evidenced by the kill curves in FIGS. 2 and 3. For example, surprising and clinically meaningful effects were seen at the following relative cannabinoid-daptomycin amounts: For CBC:Oaptomycin 1:1-4 (FIG. 3 3303 strain), 1:1-8 (FIG. 2; 58C9 Strain), and 1:4-16 (FIG. 2 55A6 Strain); For CBG:Oaptomycin 2:1 and 1:1-4 (FIG. 3 3303 Strain), 1:1-8 (FIG. 2; 58C9 Strain), and 1:2-16 (FIG. 2; 55A6 Strain); and, for CBO:Daptomycin 2:1 and 1:1-4 (FIG. 3 3303 Strain), 1:1-8 (FIG. 2; 58C9), and 1:2-16 (FIG. 2; 55A6 Strain).

Example 3: CBD and CBG Biofilm Inhibition

Figure 4:
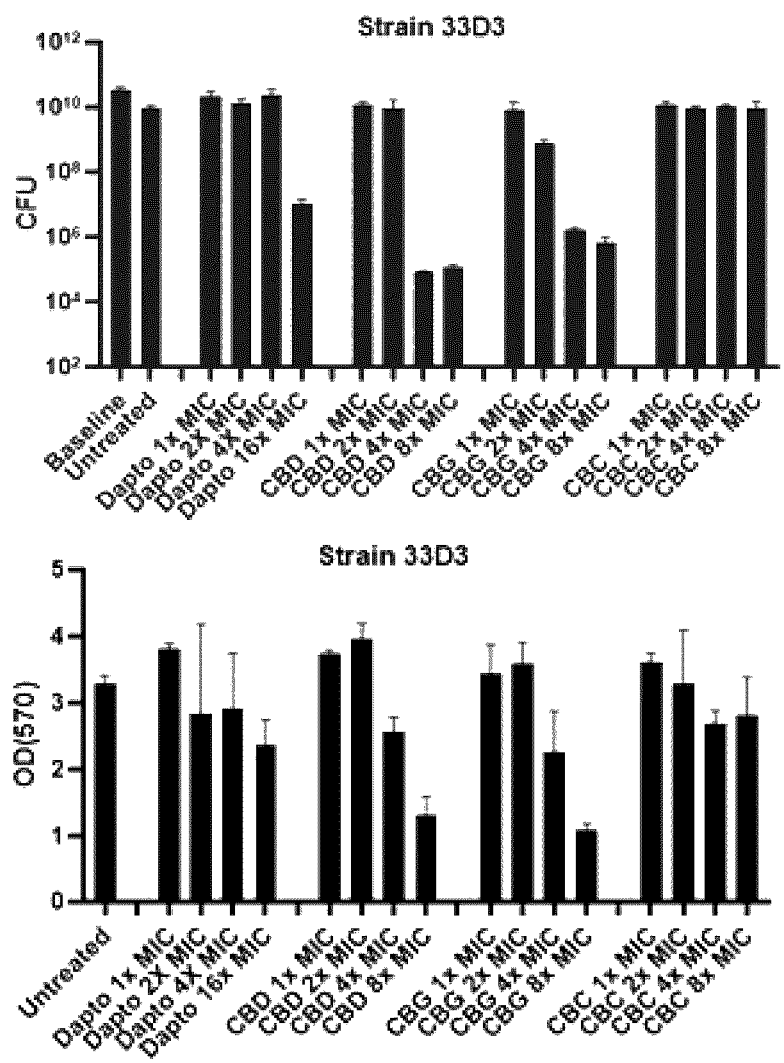
FIG. 4 includes two bar graphs, illustrating the effect of CBD, CBG and CBC on biofilms of *E. faecium* strain 3303.

This example illustrates that CBO and CBG are surprisingly effective at inhibiting *E. faecium* biofilm growth. The data in FIG. 4 was generated by growing biofilms of *E. faecium* strain 3303 for 48 h without cannabinoids, then treating the biofilms with cannabinoids for 72 h. The mass of the biofilm was quantitated by crystal violet staining. Viable bacteria in the biofilm were quantitated by scrapping biofilm then counting the viable bacteria. As illustrated, CBO and CBG illustrate a surprising degree of antibiotic activity against the strain 3303 of *E. faecium*. Of note, CBC was bactericidal against planktonic Enterococci.

REFERENCES

Abdelaziz, A, (1982) Studies on the antimicrobial activity of cannabinoids. MS thesis, Ohio State University.

Andre, C. M.; Hausman, J.-F.; Guerriero, G. (2016). "*Cannabis sativa*: The Plant of the Thousand and One Molecules". Frontiers in Plant Science. 7: 19.

Appendino, G., G. Chianese & O. Taglialatela-Scafati, (2011) Cannabinoids: occurrence and medicinal chemistry. Curr Med Chem 18: 10854099.

Appendino, G., S. Gibbons, A Giana, A Pagani, G. Grassi, M. Stavri, E. Smith & M. M. Rahman, (2008) Antibacterial cannabinoids from *Cannabis sativa*: a structure-activity study. J Nat Prod 71: 1427-1430.

Arias, C. A. & B. E. Murray, (2012) The rise of the *Enterococcus*: beyond vancomycin resistance. Nat Rev Microbial 10: 266-278.

Arias, C. A., D. Panessa, D. M. McGrath, X. Qin, M. F. Mojica, C. Miller, L. Diaz, T. T. Tran, S. Rincon, E. M.

Baltz R H (December 2006). "Molecular engineering approaches to peptide, polyketide and other antibiotics". Nature Biotechnology. 24 (12): 1533-40.

Barbu, J. Reyes, J. H. Roh, E. Lobos, E. Sodergren, R. Pasqualini, W. Arap, J. P. Quinn, Y. Shamoo, B. E. Murray & G. M. Weinstock, (2011) Genetic basis for in vivo daptomycin resistance in enterococci. N Engl. Med 365: 892-900.

Berenbaum, M. C. 1978. A method for testing for synergy with any number of agents. J. Infect. Dis. 137:122-130.

Arthur, M. & P. Courvalin, (1993) Genetics and mechanisms of glycopeptide resistance in enterococci. Antimicrob Agents Chemother 37: 1563-1571.

Consroe, P., J. Laguna, J. Allender, S. Snider, L. Stern, R. Sandyk, K. Kennedy & K. Schram, (1991) Controlled clinical trial of cannabidiol in Huntington's disease. Pharmacol Biochem Behav 40: 701-708.

Cunha, J. M., E. A. Carlini, A. E. Pereira, O. L. Ramos, C. Pimentel, R. Gagliardi, W. L. Sanvito, N. Lander & R. Mechoulam, (1980) Chronic administration of cannabidiol to healthy volunteers and epileptic patients. Pharmacology 21: 175-185.

Eisohly, H. N., C. E. Turner, A M. Clark & M. A. Eisohly, (1982) Synthesis and antimicrobial activities of certain cannabichromene and cannabigerol related compounds. J Pharm Sci 71: 1319-1323.

Galloway-Pena, J. R., S. R. Nallapareddy, C. A. Arias, G. M. Eliopoulos & B. E. Murray, (2009) Analysis of clonality and antibiotic resistance among early clinical isolates of *Enterococcus faecium* in the United States. J Infect Dis 200: 1566-1573.

Hidron, A. I., J. R. Edwards, J. Patel, T. C. Horan, D. M. Sievert, D. A. Pollock, S. K. Fridkin, T. National Healthcare Safety Network & F. Participating National Healthcare Safety Network, (2008) NHSN annual update: antimicrobial-resistant pathogens associated with healthcare-associated infections: annual summary of data reported to the National Healthcare Safety Network at the Centers for Disease Control and Prevention, 2006-2007. Infect Control Hosp Epidemiol 29: 996-1011.

Luo X, Reiter M A, d'Espaux L, Wong J, Denby C M, Lechner A, Zhang Y, Grzybowski A T, Harth S, Lin W, Lee H, Yu C, Shin J, Deng K, Benites V T, Wang G, Baidoo E E K, Chen Y, Dev I, Petzold C J, Keasling J D. 2019. Complete biosynthesis of cannabinoids and their unnatural analogues in yeast. Nature 567:123-126

Mechoulam, R. & Y. Gaoni, (1965) Hashish. IV. The isolation and structure of cannabinolic cannabidiolic and cannabigerolic acids. Tetrahedron 21: 1223-1229.

Miao V, Coeffet-Le Gal M F, Nguyen K, Brian P, Penn J, Whiting A, Steele J, Kau D, Martin S, Ford R, Gibson T, Bouchard M, Wrigley S K, Baltz R H (March 2006). "Genetic engineering in *Streptomyces roseosporus* to produce hybrid lipopeptide antibiotics". Chemistry & Biology. 13 (3): 269-76.

Morales, P., D. P. Hurst & P. H. Reggio, (2017) Molecular Targets of the Phytocannabinoids: A Complex Picture. Prog Chem Org Nat Prod 103: 103-131.

Murdoch, D. R., G. R. Corey, B. Hoen, J. M. Miro, V. G. Fowler, Jr., A S. Bayer, A W. Karchmer, L. Olaison, P. A. Pappas, P. Moreillon, S. T. Chambers, V. H. Chu, V. Falco, D. J. Holland, P. Jones, J. L. Klein, N. J. Raymond, K. M. Read, M. F. Tripodi, R. Utili, A Wang, C. W. Woods, C. H. Cabell & I. International Collaboration on Endocarditis-Prospective Cohort Study, (2009) Clinical presentation, etiology, and outcome of infective endocarditis in the 21st century: the International Collaboration on Endocarditis-Prospective Cohort Study. Arch Intern Med 169: 463-473.

Najafi K, Ganbarov K, Gholizadeh P, Tanomand A, Rezaee M A, Mahmood S S, Asgharzadeh M, Kafil H S. 2019. Oral cavity infection by *Enterococcus faecalis*: virulence factors and pathogenesis. Reviews in Medical Microbiology 29: 000 Publish Ahead of Print.

Nguyen K T, Kau D, Gu J Q, Brian P, Wrigley S K, Baltz R H, Miao V (September 2006). "A glutamic acid 3-methyltransferase encoded by an accessory gene locus important for daptomycin biosynthesis in *Streptomyces roseosporus*". Molecular Microbiology. 61 (5): 1294-307.

Nguyen, K. T., He, X., Alexander, D. C., Li, C., Gu, J. Q., Mascio, C., Van Praagh, A, Mortin, L., Chu, M., Silverman, J. A, Brian, P., & Baltz, R. H. (2010). Genetically engineered lipopeptide antibiotics related to A54145 and daptomycin with improved properties. Antimicrobial agents and chemotherapy, 54(4), 1404-1413.

Odds, F. C., Synergy, antagonism, and what the chequerboard puts between them, Journal of Antimicrobial Chemotherapy, (2003) 52, 1.

Paganelli, Fernanda L et al. "*Enterococcus faecium* biofilm formation: identification of major autolysin AtlAEfm, associated Acm surface localization, and AtlAEfm-independent extracellular DNA Release." *mBio* vol. 4.2 e00154. 16 Apr. 2013, doi:10.1128/mBio.00154-13.

Prematunge, C., C. MacDougall, J. Johnstone, K. Adomako, F. Lam, J. Robertson & G. Garber, (2016) VRE and VSE Bacteremia Outcomes in the Era of Effective VRE Therapy: A Systematic Review and Meta-analysis. Infect Control Hosp Epidemiol 37: 26-35.

Russo, E. B., (2011) Taming THC: potential cannabis synergy and phytocannabinoid-terpenoid entourage effects. Br.1 Pharmacol 163: 1344-1364.

Schleifer, K. H. & R. Kilpperbalz, (1984) Transfer of *Streptococcus-faecalis* and *Streptococcus-faecium* to the Genus *Enterococcus* Norn Rev as *Enterococcus-faecalis* Comb-Nov and *Enterococcus-faecium* Comb-Nov. Intl Syst Bacterial 34: 31-34.

Steenackers, B.; De Cooman, L.; De Vos, D. (2015). "Chemical transformations of characteristic hop secondary metabolites in relation to beer properties and the brewing process: A review". Food Chemistry. 172: 742-756.

Trost and Dogra, (2007) Synthesis of (−)-9-trans-Tetrahydrocannabinol-Stereocontrol via Mo-catalyzed Asymmetric Allylic Alkylation Reaction. Org Lett. 2007 Mar. 1; 9(5): 861-863.

Turner, C. E. & M. A. Elsohly, (1981) Biological activity of cannabichromene, its homologs and isomers. J Clin Pharmacol 21: 2835-2915. Van Klingeren, B. & M. Ten Ham, (1976) Antibacterial activity of delta9-tetrahydrocannabinol and cannabidiol. Antonie Van Leeuwenhoek 42: 9-12.

Yu, V. L., T. P. Felegie, R. B. Yee, A W. Pasculle, and F. H. Taylor. 1980. Synergistic interaction in vitro with use of three antibiotics simultaneously against *Pseudomonas maltophilia*. J. Infect. Dis. 142:602-607.

Zhong et al., (2017) Comparative genomic analysis of the genus *Enterococcus*. Microbiological Research, Volume 196, March 2017, Pages 95-105.

The invention claimed is:

1. A method of treating a Gram-positive bacterial infection in a subject in need thereof, wherein the subject is undergoing treatment with a lipopeptide antibiotic that is daptomycin, the method comprising administering to the subject
 a cannabinoid that is one or both of cannabichromene (CBC) and/or cannabigerol (CBG), wherein the cannabinoid is administered at a dosage of 0.5 mg/kg and the daptomycin is administered at a dosage ranging from 0.125 mg/kg to 8 mg/kg.

2. The method of claim 1, wherein the Gram-positive bacterial infection comprises infection by an Enterococcus faecium or an *Enterococcus faecalis*.

3. The method of claim 1, wherein the subject is a human.

4. The method of claim 1, wherein the cannabinoid is administered via parenteral administration.

5. The method of claim 1, wherein the cannabinoid is administered via intraperitoneal administration.

6. The method of claim 1, wherein the Gram-positive bacterial infection is an antibiotic resistant infection.

7. The method of claim 6, wherein the antibiotic resistant infection is a vancomycin resistant bacterial infection.

8. The method of claim 6, wherein the antibiotic resistant infection is a daptomycin resistant bacterial infection.

* * * * *